(12) United States Patent
Iyo et al.

(10) Patent No.: US 8,008,047 B2
(45) Date of Patent: Aug. 30, 2011

(54) L-AMINO ACID PRODUCING BACTERIUM WHICH HAS ENHANCED EXPRESSION OF AT LEAST ONE OF THE NHAA GENE, THE NHAB GENE, THE NHAR GENE, THE CHAA GENE, THE MDFA GENE AND A METHOD OF PRODUCING L-AMINO ACID

(75) Inventors: Mayu Iyo, Kawasaki (JP); Ryo Takeshita, Kawasaki (JP); Shinichi Sugimoto, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 134 days.

(21) Appl. No.: 12/137,666

(22) Filed: Jun. 12, 2008

(65) Prior Publication Data

US 2009/0258401 A1 Oct. 15, 2009

Related U.S. Application Data

(63) Continuation of application No. PCT/JP2006/325452, filed on Dec. 14, 2006.

(30) Foreign Application Priority Data

Dec. 16, 2005 (JP) .................................. 2005-363120
Aug. 4, 2006 (JP) .................................. 2006-213578

(51) Int. Cl.
*C12P 13/04* (2006.01)
*C12P 13/08* (2006.01)
*C12N 1/20* (2006.01)
*C12N 15/00* (2006.01)
*C07H 21/04* (2006.01)

(52) U.S. Cl. ...................... 435/106; 435/115; 435/252.3; 435/320.1; 536/23.2

(58) Field of Classification Search ........................ None
See application file for complete search history.

(56) References Cited

U.S. PATENT DOCUMENTS

| | | | |
|---|---|---|---|
| 5,661,012 A | 8/1997 | Sano et al. | |
| 5,827,698 A | 10/1998 | Kikuchi et al. | |
| 5,830,716 A | 11/1998 | Kojima et al. | |
| 5,932,453 A | 8/1999 | Kikuchi et al. | |
| 5,972,663 A * | 10/1999 | Winterhalter et al. | 435/113 |
| 6,040,160 A | 3/2000 | Kojima et al. | |
| 6,878,533 B2 | 4/2005 | Tsujimoto et al. | |
| 6,905,819 B1 | 6/2005 | Matsuzaki et al. | |
| 6,911,332 B2 | 6/2005 | Usuda et al. | |
| 7,026,149 B2 | 4/2006 | Usuda et al. | |
| 7,029,893 B2 | 4/2006 | Usuda et al. | |
| 7,060,475 B2 | 6/2006 | Usuda et al. | |
| 7,160,704 B2 | 1/2007 | Takeshita et al. | |
| 7,192,747 B2 | 3/2007 | Ono et al. | |
| 7,192,748 B2 | 3/2007 | Usuda et al. | |
| 7,211,421 B2 | 5/2007 | Tsujimoto | |
| 7,220,570 B2 | 5/2007 | Usuda et al. | |
| 7,223,572 B1 | 5/2007 | Gunji et al. | |
| 7,244,569 B2 | 7/2007 | Matsuzaki et al. | |
| 7,306,933 B2 | 12/2007 | Dien et al. | |
| 2002/0025564 A1 | 2/2002 | Kobayashi et al. | |
| 2002/0155556 A1 | 10/2002 | Imaizumi et al. | |
| 2002/0160461 A1 | 10/2002 | Nakai et al. | |
| 2004/0229305 A1 | 11/2004 | Usuda et al. | |
| 2005/0176121 A1 | 8/2005 | Takeshita et al. | |
| 2006/0019355 A1 | 1/2006 | Ueda et al. | |
| 2006/0019356 A1 | 1/2006 | Usuda et al. | |
| 2006/0030010 A1 | 2/2006 | Usuda et al. | |
| 2006/0030011 A1 | 2/2006 | Usuda et al. | |
| 2007/0243590 A1 | 10/2007 | Takeshita et al. | |
| 2007/0249017 A1 | 10/2007 | Usuda et al. | |
| 2008/0038825 A1 | 2/2008 | Gunji et al. | |

FOREIGN PATENT DOCUMENTS

| | | |
|---|---|---|
| EP | 1 108 790 | 6/2001 |
| EP | 1 700 864 | 9/2006 |
| WO | WO01/53459 | 7/2001 |
| WO | WO2006/038695 | 4/2006 |
| WO | WO2006/123764 | 11/2006 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Mine et al. J Biochem. Jul. 1998;124(1):187-93.*
Accession P0A9G2. Published Jul. 19, 2005.*
Accession AF387550. Published May 10, 2004.*
Lewinson, O., et al., "Alkalitolerance: A biological function for a multidrug transporter in pH homeostasis," PNAS 2004;101(39):14073-14078.
Nilsen, I. W., et al., "Isolation of *cmr*, a Novel *Escherichia coli* Chloramphenicol Resistance Gene Encoding a Putative Efflux Pump," J. Bacteriol. 1996;178(11):3188-3193.
Padan, E., et al., "$Na^+/H^+$ antiporters," Biochemica et Biophysica Acta 2001;1505:144-157.
International Search Report and Written Opinion of the International Searching Authority for PCT Patent App. No. PCT/JP2006/325452 (Apr. 11, 2007).
Adler, J., et al., "Determinants of Substrate Recognition by the *Escherichia coli* Multidrug Transporter MdfA Identified on Both Sides of the Membrane," J. Biol. Chem. 2004;279(10):8957-8965.
Carmel, O., et al., "The $Na^+$-specific interaction between the LysR-type regulator, NhaR, and the *nhaA* gene encoding the $Na^+/H^+$ antiporter of *Escherichia coil*," The EMBO Journal 1997;16(19):5922-5929.
Kegg, *Escherichia coli* K-12 MG1655: b0019, pp. 1-2, (Printed Aug. 1, 2008).
Kegg. *Escherichia coli* K-12 MG1655: b1186, pp. 1-2, (Printed Aug. 1, 2008).
Kegg, *Escherichia coli* K-12 MG1655: b0020, p. 1, (Printed Aug. 1, 2008).

(Continued)

*Primary Examiner* — Christian Fronda
(74) *Attorney, Agent, or Firm* — Shelly Guest Cermak; Cermak Nakajima LLP

(57) ABSTRACT

L-amino acid is produced by culturing a bacterium belonging to the Enterobacteriaceae family which has L-amino acid-producing ability and is modified so that expression of the nhaA gene, nhaB gene, nhaR gene, chaA gene, mdfA gene, or combinations thereof is enhanced.

7 Claims, No Drawings

OTHER PUBLICATIONS

Kegg, *Escherichia coli* K-12 MG1655: b1216, pp. 1-2, (Printed Aug. 1, 2008).

Kegg, *Escherichia coli* K-12 MG1655: b0842, pp. 1-2, (Printed Aug. 1, 2008).

Shijuku, T., et al., "Expression of *chaA*, a sodium ion extrusion system of *Escherichia coil*, is regulated by osmolarity and pH," Biochimica et Biophysica Acta 2002;1556:142-148.

Zuber, D., et al., "Kinetics of charge translocation in the passive downhill uptake mode of the $Na^{30}/H^+$ antiporter NhaA of *Escherichia coil*," Biochimica et Biophysica Acta 2005;1709:240-250.

International Prelimin Report of Patentability and Written Opinion Of The International Searching Authority for PCT Patent App. No. PCT/JP2006/325452 (Jun. 26, 2008).

* cited by examiner

L-AMINO ACID PRODUCING BACTERIUM WHICH HAS ENHANCED EXPRESSION OF AT LEAST ONE OF THE NHAA GENE, THE NHAB GENE, THE NHAR GENE, THE CHAA GENE, THE MDFA GENE AND A METHOD OF PRODUCING L-AMINO ACID

The present application is a continuation of PCT Patent Application No. PCT/JP2006/325452, filed on Dec. 14, 2006, which claims priority under 35 U.S.C. §119 to Japanese Patent Application No. 2005-363120, filed on Dec. 16, 2005, and Japanese Patent Application No. 2006-213578, filed on Aug. 4, 2006, the entireties of which are incorporated by reference. Also, the Sequence Listing filed electronically via EFS-Web herewith is hereby incorporated by reference (File name: US-315_Seq_List_Copy_1; File size: 86 KB; Date recorded: Jun. 12, 2008).

BACKGROUND OF THE INVENTION

1. Field of the Invention

The present invention relates to a method of producing an L-amino acid using a bacterium, and more specifically, to a method of producing L-lysine, L-threonine and L-glutamic acid. L-lysine and L-threonine are useful as additives for animal feeds, components of health foods, amino acid infusion, and the like. L-glutamic acid is useful as a food seasoning.

2. Brief Description of the Related Art

L-amino acids are industrially produced by fermentation methods using bacteria belonging to the genus *Brevibacterium*, *Corynebacterium*, *Escherichia*, and the like. Examples of a method of producing L-lysine include the methods described in EP 0643135 B, EP 0733712 B, EP 1477565 A, EP 0796912 A, EP 0837134 A, WO 01/53459, EP 1170376 A, and WO 2005/010175. In these production methods, bacterial strains isolated from nature or artificially mutated strains thereof can be used. Also, bacteria which have been modified by a recombinant DNA technique so that the activity of an L-amino acid biosynthetic enzyme is enhanced have been used.

Methods of modifying the uptake or export of L-amino acids have been known to improve L-amino acid-producing ability. An example of a method of enhancing export of an L-amino acid is a method of producing L-lysine (WO 97/23597) or L-arginine (U.S. Patent Publication No. 2003-0113899) using a bacterium belonging to the genus *Corynebacterium* which has been modified so that the expression of an L-lysine/L-arginine export gene (LysE) is enhanced. In addition, a method of producing an L-amino acid using a bacterium belonging to the Enterobacteriaceae family which has been modified so that expression of the rhtA gene, rhtB gene, and rhtC gene (JP 2000-189177 A), yfiK gene and yahN gene (EP 1016710 A), ybjE gene (WO 2005/073390), or yhfK gene (WO 2005/085419), have been reported, and it has been suggested that such methods are involved in enhanced export of an L-amino acid.

It is also known that enhancing expression of a gene involved in the uptake of a sugar which is a substrate in fermentation improves the L-amino acid-producing ability. Examples of such a method include producing an L-amino acid using an *Escherichia* bacterium which has been modified to enhance expression of the ptsG gene (WO 03/04670), and producing an L-amino acid using an *Escherichia* bacterium modified to enhance expression of the ptsH gene, ptsI gene, or crr gene (WO 03/04674).

The nhaA gene and nhaB gene each encode a membrane protein known as the $Na^+/H^+$ antiporter (Biochim Biophys Acta. 2005 Sep. 30; 1709 (3): 240-50.). On the other hand, the nhaR gene is known to encode a regulator that positively regulates expression of the nhaA gene (EMBO J. 1997 Oct. 1; 16(19): 5922-9.). However, whether or not enhancing the activity of the $Na^+/H^+$ antiporter has an effect on L-amino acid production has not been previously reported.

The chaA gene is a membrane protein which is known as a sodium-calcium/proton antiporter, but it has never been reported to have an $Na^+/H^+$ antiporter function (Biochim Biophys Acta. 2002 Dec. 2; 1556 (2-3): 142-8.). The mdfA gene is known to function as a multidrug/chloramphenicol efflux transporter (J Biol Chem. 2004 Mar. 5; 279(10): 8957-65), but it has never been reported to have an $Na^+/H^+$ antiporter function, and the involvement of these genes in the production and accumulation of L-amino acids has not been reported.

SUMMARY OF THE INVENTION

An aspect of the present invention is to provide a bacterium which is capable of effectively producing an L-amino acid and to provide a method for effectively producing an L-amino acid using the bacterium.

The inventors have found that L-amino acid productivity is improved by amplifying genes that encode a $Na^+/H^+$ antiporter or a gene that positively regulates $Na^+/H^+$ antiporter activity in an L-amino acid-producing bacterium. Moreover, they have found that enhancing the $Na^+/H^+$ antiporter activity in a bacterium results in efficient production of an L-amino acid.

It is an aspect of the present invention to provide an L-amino acid-producing bacterium belonging to the Enterobacteriaceae family, wherein said bacterium has been modified so that $Na^+/H^+$ antiporter activity is enhanced.

It is a further aspect of the present invention to provide the bacterium as described above, wherein said $Na^+/H^+$ antiporter activity is enhanced by modifying said bacterium so that expression of a gene selected from the group consisting of nhaA gene, nhaB gene, nhaR gene, chaA gene, mdfA gene, and combinations thereof, is enhanced.

It is a further aspect of the present invention to provide the bacterium as described above, wherein said expression is enhanced by increasing the copy number of the gene or genes, or by modifying an expression regulatory sequence of the gene or genes.

It is a further aspect of the present invention to provide the bacterium as described above, wherein said nhaA gene encodes a protein selected from the group consisting of:

(A) a protein comprising the amino acid sequence of SEQ ID NO: 2, and (B) a protein comprising an amino acid sequence which includes substitution, deletion, insertion or addition of one or several amino acids in SEQ ID NO: 2, and has $Na^+/H^+$ antiporter activity.

It is a further aspect of the present invention to provide the bacterium as described above, wherein said nhaB gene encodes a protein selected from the group consisting of:

(C) a protein comprising the amino acid sequence of SEQ ID NO: 4, and (D) a protein comprising an amino acid sequence which includes substitution, deletion, insertion or addition of one or several amino acids in SEQ ID NO: 4, and has $Na^+/H^+$ antiporter activity.

It is a further aspect of the present invention to provide the bacterium as described above, wherein said nhaR gene encodes a protein selected from the group consisting of:

(E) a protein comprising the amino acid sequence of SEQ ID NO: 6; and (F) a protein comprising an amino acid sequence which includes substitution, deletion, insertion or addition of one or several amino acids in SEQ ID NO: 6, and has an activity to increase expression of $Na^+/H^+$ antiporter.

It is a further aspect of the present invention to provide the bacterium as described above, wherein said chaA gene encodes a protein selected from the group consisting of:

(G) a protein comprising the amino acid sequence of SEQ ID NO: 24; and (H) a protein comprising an amino acid sequence which includes substitution, deletion, insertion or addition of one or several amino acids in SEQ ID NO: 24, and has $Na^+/H^+$ antiporter activity.

It is a further aspect of the present invention to provide the bacterium as described above, wherein said mdfA gene encodes a protein selected from the group consisting of:

(I) a protein comprising the amino acid sequence of SEQ ID NO: 26; and (J) a protein comprising an amino acid sequence including substitution, deletion, insertion or addition of one or several amino acids in SEQ ID NO: 26, and has $Na^+/H^+$ antiporter activity.

It is a further aspect of the present invention to provide the bacterium as described above, wherein said nhaA gene is a DNA selected from the group consisting of:

(a) a DNA comprising the nucleotide sequence of SEQ ID NO: 1; and (b) a DNA that hybridizes with a complementary strand of the nucleotide sequence of SEQ ID NO: 1 or a probe prepared from the nucleotide sequence under stringent conditions, and wherein said DNA encodes a protein that has $Na^+/H^+$ antiporter activity.

It is a further aspect of the present invention to provide the bacterium as described above, wherein said nhaB gene is a DNA selected from the group consisting of:

(c) a DNA comprising a nucleotide sequence shown in SEQ ID NO: 3; and (d) a DNA that hybridizes with a complementary strand of the nucleotide sequence of SEQ ID NO: 3 or a probe prepared from the nucleotide sequence under stringent conditions, and wherein said DNA encodes a protein that has $Na^+/H^+$ antiporter activity.

It is a further aspect of the present invention to provide the bacterium as described above, wherein said nhaR gene is a DNA selected from the group consisting of:

(e) a DNA comprising a nucleotide sequence shown in SEQ ID NO: 5; and (f) a DNA that hybridizes with a complementary strand of the nucleotide sequence of SEQ ID NO: 5 or a probe prepared from the nucleotide sequence under stringent conditions, and wherein said DNA encodes a protein that has an activity to increase expression of $Na^+/H^+$ antiporter.

It is a further aspect of the present invention to provide the bacterium as described above, wherein said chaA gene is a DNA selected from the group consisting of:

(g) a DNA comprising a nucleotide sequence shown in SEQ ID NO: 23; and (h) a DNA that hybridizes with a complementary strand of the nucleotide sequence of SEQ ID NO: 23 or a probe prepared from the nucleotide sequence under stringent conditions, and wherein said DNA encodes a protein that has $Na^+/H^+$ antiporter activity.

It is a further aspect of the present invention to provide the bacterium as described above, wherein said mdfA gene is a DNA selected from the group consisting of:

(i) a DNA comprising a nucleotide sequence shown in SEQ ID NO: 25; and (j) a DNA that hybridizes with a complementary strand of the nucleotide sequence of SEQ ID NO: 25 or a probe prepared from the nucleotide sequence under stringent conditions, and wherein said DNA encodes a protein that has $Na^+/H^+$ antiporter activity.

It is a further aspect of the present invention to provide the bacterium as described above, wherein said L-amino acid is selected from the group consisting of L-lysine, L-arginine, L-histidine, L-isoleucine, L-valine, L-leucine, L-threonine, L-phenylalanine, L-tyrosine, L-tryptophan, L-cysteine, L-glutamic acid, and combinations thereof.

It is a further aspect of the present invention to provide the bacterium as described above, wherein said bacterium belongs to the genus *Escherichia* or *Pantoea*.

It is a further aspect of the present invention to provide a method of producing an L-amino acid comprising culturing the bacterium as described above in a medium to produce and accumulate an L-amino acid in the medium or cells of the bacterium and collecting the L-amino acid from the medium or the cells.

It is a further aspect of the present invention to provide the method as described above, wherein said L-amino acid is selected from the group consisting of L-lysine, L-arginine, L-histidine, L-isoleucine, L-valine, L-leucine, L-threonine, L-phenylalanine, L-tyrosine, L-tryptophan, L-cysteine, L-glutamic acid, and combinations thereof.

DESCRIPTION OF THE PREFERRED EMBODIMENTS

Hereinafter, the present invention will be described in detail.

<1> Bacterium of the Present Invention

The bacterium of the present invention belongs to the Enterobacteriaceae family and has an L-amino acid-producing ability. This bacterium also is modified so that the $Na^+/H^+$ antiporter activity is enhanced. The term "L-amino acid-producing ability" means an ability to produce and accumulate an L-amino acid in a medium or bacterial cells when the bacterium is cultured in the medium. The bacterium may produce a plurality of L-amino acids. The ability may be native to the bacterium, or the ability may be obtained by modifying the bacterium by mutation and or with recombinant DNA techniques.

The L-amino acid is not particularly limited, but examples include basic amino acids such as L-lysine, L-ornithine, L-arginine, L-histidine, and L-citrulline, aliphatic amino acids such as L-isoleucine, L-alanine, L-valine, L-leucine, and L-glycine, hydroxy monoaminocarboxylic acid such as L-threonine and L-serine, cyclic amino acids such as L-proline, aromatic amino acids such as L-phenylalanine, L-tyrosine, and L-tryptophan, sulfur-containing amino acids such as L-cysteine, L-cystine, and L-methionine, and acidic amino acids such as L-glutamic acid, L-aspartic acid, L-glutamine, and L-asparagine. The bacterium may produce two or more kinds of amino acids.

<1-1> Imparting L-Amino Acid-Producing Ability

Hereinafter, examples of methods for imparting the ability to produce L-amino acids and examples of the bacteria to which such an ability can be imparted will be described. However, the bacterium is not limited thereto, as long as it has an L-amino acid-producing ability.

Bacteria belonging to the Enterobacteriaceae family, including those belonging to the genus *Escherichia* or *Pantoea*, can be used as the parent strain of the bacterium of the present invention. Other examples of bacteria belonging to the Enterobacteriaceae family include γ-Proteobacteria such as *Enterobacter, Klebsiella, Serratia, Erwinia, Salmonella*, and *Morganella*.

*Escherichia* bacteria reported in Neidhardt et al. ((Backmann, B. J. 1996. Derivations and Genotypes of some mutant derivatives of *Escherichia coli* K-12, p. 2460-2488. Table 1. In F. D. Neidhardt (ed.), *Escherichia coli* and *Salmonella* Cellular and Molecular Biology/Second Edition, American Society for Microbiology Press, Washington, D.C.), such as *Escherichia coli* can be utilized. Examples of a wild-type strain of *Escherichia coli* include the K-12 strain or derivatives thereof, *Escherichia coli* MG1655 strain (ATCC No. 47076), and W3110 strain (ATCC No. 27325). These strains are available from the American Type Culture Collection (ATCC) (Address: P.O. Box 1549, Manassas, Va. 20108, 1, United States of America).

Examples of *Enterobacter* bacteria include *Enterobacter agglomerans* and *Enterobacter aerogenes*, and an example of *Pantoea* bacteria is *Pantoea ananatis*. In recent years, *Enterobacter agglomerans* has been reclassified in some cases as *Pantoea agglomerans, Pantoea ananatis, Pantoea stewartii*, or the like based on an analysis of the nucleotide sequence of 16S rRNA. Therefore, bacteria to be used in the present invention may belong to either the genus *Enterobacter* or the genus *Pantoea* as long as they are classified in the Enterobacteriaceae family. When *Pantoea ananatis* is bred using genetic engineering techniques, *Pantoea ananatis* AJ13355 (FERM BP-6614), AJ13356 (FERM BP-6615), AJ13601 (FERM BP-7207), derivatives thereof, and the like, may be used. These strains were identified and deposited as *Enterobacter agglomerans* when they were isolated, but as described above, these strains have been reclassified as *Pantoea ananatis* based on an analysis of the nucleotide sequence of 16S rRNA.

The L-amino acid-producing ability can be imparted to a parent strain as described above, as follows.

In order to impart the L-amino acid-producing ability, methods which have been conventionally adopted in the breeding of *Escherichia* bacteria or the like, may be used, such as by acquiring nutrient-auxotrophic mutant strains, analogue resistant strains, or metabolic regulation mutant strains, or by creating a recombinant strain in which expression of an L-amino acid biosynthetic enzyme is enhanced (Amino Acid Fermentation, Japan Scientific Societies Press, first edition publication: May 30, 1986, p. 77 to 100). In the present invention, properties such as nutrient-auxotrophy, analogue-resistance, and metabolic regulation may be imparted alone or in combination with the imparting of L-amino acid-producing ability. Furthermore, expression of one or more L-amino acid biosynthetic enzymes may be enhanced. Furthermore, imparting of such properties as nutrient-auxotrophy, analogue-resistance and metabolic regulation mutation may be combined with enhancing the expression of L-amino acid biosynthetic enzymes.

Nutrient-auxotrophic mutant strains, L-amino acid-analogue resistant strains, and metabolic regulation mutant strains that have an L-amino acid-producing ability can be obtained as follows. A parent strain or a wild-type strain is mutated by a typical mutation treatment, such as irradiation with X-ray or ultraviolet ray or by treating with a mutagen, including N-methyl-N'-nitro-N-nitrosoguanidine (NTG) and ethylmethanesulfonate (EMS), followed by selection of strains that exhibit nutrient-auxotrophy, analogue-resistance or a metabolic regulation mutation and have an L-amino acid-producing ability.

Examples of an L-lysine analogue include oxalysine, lysinehydroxamate, S-(2-aminoethyl)-L-cysteine (AEC), γ-methyllysine, α-chlorocaprolactam, and norleucine. Examples of an L-arginine analogue include arginine hydroxamate, homoarginine, D-arginine, and canavanine.

Specific examples of an L-lysine analogue resistant strain or metabolic regulation mutant strain having an L-lysine-producing ability include *Escherichia coli* AJ11442 strain (FERM BP-1543, NRRL B-12185; JP 56-18596 A and U.S. Pat. No. 4,346,170) and *Escherichia coli* VL611 strain (JP 2000-189180 A). WC196 strain (WO 96/17930) may be used as an L-lysine producing strain of *Escherichia coli*. WC196 strain has been obtained by imparting AEC(S-(2-aminoethyl)-cysteine)-resistance to W310 strain which was derived from *Escherichia coli* K-12 strain. The WC196 strain was named *Escherichia coli* AJ13069 strain and deposited at the National Institute of Bioscience and Human-Technology, Agency of Industrial Science and Technology (currently, International Patent Organism Depositary, National Institute of Advanced Industrial Science and Technology, Central 6, 1-1-1 Higashi, Tsukuba, Ibaraki 305-8566, Japan) on Dec. 6, 1994 and given an accession number of FERM P-14690, and the deposit was then converted to an international deposit under the provisions of Budapest Treaty on Sep. 29, 1995 and given an accession number of FERM BP-5252.

An L-amino acid-producing ability can also be imparted by enhancing the expression of a gene encoding an L-amino acid biosynthetic enzyme.

For example, as described below, an L-lysine-producing ability may be imparted by enhancing the activities of dihydrodipicolinate synthase and aspartokinase. That is, a gene fragment encoding dihydrodipicolinate synthase and a gene fragment encoding aspartokinase are ligated to a vector which functions in a host bacterium to be used for L-lysine production. The vector is preferably a multi-copy vector, and the obtained vector DNA is used to transform a host bacterium. The transformation results in increased copy numbers of the gene encoding the dihydrodipicolinate synthase and the gene encoding aspartokinase in a host cell, thereby enhancing the activities of these enzymes. Hereinafter, dihydrodipicolinate synthase, aspartokinase, and aspartokinase III are abbreviated as DDPS, AK, and AKIII, respectively.

The gene encoding DDPS and the gene encoding AK are not particularly limited as long as the DDPS and AK activities are expressed in the host bacterium, and examples thereof include the genes of *Escherichia coli, Methylophilus methylotrophus, Corynebacterium glutamicum*, and the like. Nucleotide sequences of the DDPS gene derived from an *Escherichia* bacterium (dapA, Richaud, F. et al. J. Bacteriol., 297 (1986)) and the AKIII gene derived from an *Escherichia* bacterium (lysC, Cassan, M., Parsot, C., Cohen, G. N. and Patte, J. C., J. Biol. Chem., 261, 1052 (1986)) have been identified, so these genes can be obtained by PCR using primers synthesized based on their nucleotide sequences and the chromosomal DNA of a bacterium such as *Escherichia coli* K-12 as a template. Hereinafter, dapA and lysC derived from *Escherichia coli* will be taken as an example, but a gene encoding DDPS and a gene encoding AK are not limited thereto.

It is known that wild-type DDPS derived from *Escherichia coli* is regulated by feedback inhibition by L-lysine, while wild-type AKIII derived from *Escherichia coli* is regulated by suppression and feedback inhibition by L-lysine. Therefore, when using dapA and lysC, mutated forms of these genes are preferably used so that the genes are not subject to feedback inhibition. Hereinafter, the mutant DDPS which is not subject to feedback inhibition by L-lysine is referred to as "mutant DDPS", and the DNA encoding the mutant DDPS is referred to as "mutant dapA or dapA*". Similarly, the mutant AKIII derived from *Escherichia coli* which is not subject to feedback inhibition by L-lysine is referred to as "mutant AKIII", and the DNA encoding the mutant AKIII is referred to as "mutant lysC". However, the DDPS and AK which can be used in the present invention are not necessarily these type of mutants since DDPS derived from *Corynebacterium* bacterium is not subject to feedback inhibition.

An example of a DNA encoding mutant DDPS not subject to feedback inhibition by L-lysine includes a DNA encoding a DDPS which has an amino acid sequence in which the histidine at position 118 is substituted with tyrosine. Meanwhile, an example of a DNA encoding mutant AKIII not subject to feedback inhibition by L-lysine includes a DNA encoding an AKIII having an amino acid sequence in which the threonine at position 352, the glycine at position 323, and the methionine at position 318 are substituted with isoleucine, asparagine and isoleucine, respectively (U.S. Pat. Nos. 5,661,012 and 6,040,160). Such mutant DNAs can be obtained by a site-specific mutation using PCR or the like.

Enhancing expression of the L-lysine biosynthetic genes as described above can be attained by transformation or homologous recombination using a plasmid or the like, in the same way as the nhaA gene, nhaB gene, nhaR gene, chaA gene, and mdfA gene described below.

Wide host-range plasmids RSFD80, pCAB1, and pCABD2 are known to contain a mutant dapA gene encoding a mutant DDPS and a mutant lysC gene encoding a mutant AKIII (U.S. Pat. No. 6,040,160). *Escherichia coli* JM109 strain transformed with RSFD80 was named AJ12396 (U.S. Pat. No. 6,040,160), and the strain was deposited at the National Institute of Bioscience and Human-Technology, Agency of Industrial Science and Technology, Ministry of International Trade and Industry (currently, International Patent Organism Depositary, National Institute of Advanced Industrial Science and Technology) on Oct. 28, 1993 and given an accession number of FERM P-13936, and the deposit was then converted to an international deposit under the provisions of Budapest Treaty on Nov. 1, 1994 and given an accession number of FERM BP-4859. RSFD80 can be obtained from AJ12396 strain by a conventional method.

An L-lysine-producing ability can also be imparted by enhancing expression of genes encoding enzymes, other than DDPS and AK, which are involved in biosynthesis of L-lysine. Examples of such enzymes include enzymes in the diaminopimelate pathway such as dihydrodipicolinate reductase (dapB: hereinafter, the words in parentheses represent the gene names), diaminopimelate decarboxylase (lysA), diaminopimelate dehydrogenase (ddh) (WO96/40934), phosphoenolpyruvate carboxylase (pepC) (JP 60-87788 A), aspartate aminotransferase (aspC) (JP 06-102028 B), diaminopimelate epimerase gene (dapF) (JP 2003-135066), aspartate semialdehyde dehydrogenase (asd) (WO 00/61723), tetrahydrodipicolinate succinylase (dapD), and succinyl-diaminopimelate deacylase (dapE); or enzymes in the aminoadipic acid pathway such as homoaconitate hydratase (JP 2000-157276 A). The documents indicated in parentheses disclose L-lysine-producing strains in which expression of a gene encoding each enzyme is enhanced. The enhancement of expression of a gene encoding each enzyme may be combined with the enhancement of expression of the DDPS gene and AK gene.

Expression of genes other than L-lysine biosynthetic genes may also be enhanced to impart L-lysine-producing ability, and examples of such genes include those encoding enzymes involved in sugar uptake, sugar metabolism (glycolytic pathway), the TCA cycle, the pentose phosphate cycle, complementary pathway, and energy metabolism. Moreover, expression of genes that impart an amino acid-resistance to a host bacterium, genes encoding amino acid-export enzymes, and genes encoding enzymes involved in uptake of by-products may be enhanced.

Genes involved in sugar metabolism include genes encoding enzymes in the glycolytic pathway or enzymes involved in sugar uptake. Examples thereof include the glucose-6-phosphate isomerase gene (pgi; WO 01/02542), phosphoenolpyruvate synthase gene (pps; EP 877090 A), phosphoglucomutase gene (pgm; WO 03/04598), fructose bisphosphate aldolase gene (fbp; WO 03/04664), pyruvate kinase gene (pykF; WO 03/008609), transaldolase gene (talB; WO 03/008611), fumarase gene (fum; WO 01/02545), phosphoenolpyruvate synthase gene (pps; EP 877090 A), non-PTS sucrose uptake gene (csc; EP 149911 A), sucrose-assimilating gene (scrAB operon; WO 90/04636), PTS glucose uptake gene (ptsG, ptsH, ptsI, crr; WO 03/04670, WO 03/04674, and EP 1254957 A), and a gene involved in maltose transport (malK; EP 1254957).

Examples of genes encoding TCA cycle enzymes include citrate synthase gene (gltA; WO 03/008607), isocitrate dehydrogenase gene (icd; WO 03/008607), 2-ketoglutarate dehydrogenase gene (sucAB; WO 03/008614), and succinate dehydrogenase gene (sdh; WO 01/02544), glutamate dehydrogenase gene (gdh; U.S. Pat. No. 6,004,773).

Examples of genes encoding pentose phosphate cycle enzymes include glucose-6-phosphate dehydrogenase gene (zwf; WO 03/008607) and ribose-5-phosphate isomerase gene (rpiB; WO 03/008607).

Examples of genes encoding anaplerotic pathway include the phosphoenolpyruvate carboxylase gene (pepC; U.S. Pat. No. 5,876,983), pyruvate carboxylase gene (pyc; EP 1092776), malate dehydrogenase gene (mdh; WO 01/02546), and pyruvate decarboxylase gene (pckA; WO 04/090125).

Examples of genes encoding enzymes involved in energy metabolism include the transhydrogenase gene (pntAB; U.S. Pat. No. 5,830,716) and cytochromoe bo type oxidase gene (cyoB; EP 1070376).

Examples of genes that impart L-amino acid-resistance include the rhtB gene (U.S. Pat. No. 6,887,691), rhtC gene (EP 1013765), yedA gene (EP 1449917), yddG gene (EP 1449918), ygaZH gene (EP 1239041), yahN, yfiK, and yeaS genes (EP 1016710), rhtA gene (Res Microbiol. 2003 March; 154(2): 123-35.), and ybjE gene (WO 2005/073390).

Furthermore, in the bacterium of the present invention, an activity of an enzyme that catalyzes a reaction which branches off from L-lysine biosynthetic pathway and produces a compound other than L-lysine may be decreased or may be made deficient. Examples of such an enzyme include homoserine dehydrogenase, lysine decarboxylase, and malic enzyme, and strains in which activities of such enzymes are decreased or deficient are described in WO 95/23864, WO 96/17930, WO 2005/010175, and the like. In *Escherichia coli*, lysine decarboxylases are encoded by a cadA gene (Genbank Accession No. NP_418555, SEQ ID NO: 19) and ldcC gene (Genbank Accession No. NP_414728, SEQ ID NO: 21) (WO 96/17930), so these genes may be disrupted to enhance L-lysine-producing ability. DNA molecules homologous to the cadA gene and ldcC gene may be used as long as they can cause homologous recombination with the cadA gene and ldcC gene on the chromosome of a host bacterium. For example, a DNA molecule homologous to the cadA gene may hybridize to a complementary strand of SEQ ID NO: 19 under stringent conditions, and a DNA molecule homologous to the ldcC gene may hybridize to a complementary strand of SEQ ID NO: 21 under stringent conditions.

Activities of these enzymes can be decreased or eliminated by introducing a mutation to the genes encoding the enzymes on the chromosome using a known mutation treatment, to thereby decrease or eliminate the activities of the enzymes in a cell. For example, decreasing or eliminating the activities of the enzymes can be attained by disrupting the genes encoding the enzymes on the chromosome by gene recombination or by modifying an expression regulatory sequence such as a promoter or Shine-Dalgarno (SD) sequence. In addition, this can also be attained by introducing an amino acid substitution (missense mutation) to the region encoding the enzymes on the chromosome, introducing a stop codon (nonsense mutation), introducing a frameshift mutation that adds or deletes one or two nucleotides, or deleting part of the gene (Journal of biological Chemistry 272: 8611-8617 (1997). Meanwhile, the activities of the enzymes can also be decreased or eliminated by constructing a mutant gene encoding a mutant enzyme which has a deletion in the coding region, and then replacing the normal gene on the chromosome with the mutant gene by homologous recombination, or introducing the mutant gene using a transposon or an IS factor.

For example, the following gene recombination method can be used to introduce a mutation that decreases or eliminates the activities of the above-mentioned enzymes. A mutant gene is prepared by modifying a partial sequence of a target gene so that it does not encode an enzyme that can function normally. Then, a bacterium belonging to the Enterobacteriaceae family is transformed with a DNA containing the mutant gene to cause recombination of a gene on the bacterial chromosome with the mutant gene, thereby substituting the target gene on the chromosome with the mutant gene. Examples of this type of gene substitution using homologous recombination include the method using a linear DNA called "Red-driven integration" (Datsenko, K. A, and Wanner, B. L. Proc. Natl. Acad. Sci. USA. 97: 6640-6645 (2000), a combination of Red-driven integration and a cleavage system derived from λ phage (Cho, E. H., Gumport, R. I., Gardner, J. F. J. Bacteriol. 184: 5200-5203 (2002)) (WO 2005/010175), a method using a plasmid containing a temperature-sensitive replication origin (Datsenko, K. A, and Wanner, B. L. Proc. Natl. Acad. Sci. USA. 97: 6640-6645 (2000); U.S. Pat. No. 6,303,383; JP 05-007491 A), and the like. Meanwhile, a site-specific mutation by gene substitution using homologous recombination can also be performed by using a plasmid which is not able to replicate in a host cell.

The above-described methods for enhancing the expression of the L-lysine biosynthetic enzymes' genes and for decreasing the activities of enzymes can also be applied to genes encoding other L-amino acid synthetic enzymes so that the ability to produce another L-amino acid is imparted to a bacterium of the Enterobacteriaceae family.

Hereinafter, a bacterium to which an ability to produce an L-amino acid other than L-lysine is imparted will be exemplified.

L-Threonine-Producing Bacteria

Examples of parent strains for deriving the L-threonine-producing bacteria of the present invention include, but are not limited to, strains belonging to the genus *Escherichia*, such as *E. coli* TDH-6/pVIC40 (VKPM B-3996) (U.S. Pat. No. 5,175,107, U.S. Pat. No. 5,705,371), *E. coli* 472T23/pYN7 (ATCC 98081) (U.S. Pat. No. 5,631,157), *E. coli* NRRL-21593 (U.S. Pat. No. 5,939,307), *E. coli* FERM BP-3756 (U.S. Pat. No. 5,474,918), *E. coli* FERM BP-3519 and FERM BP-3520 (U.S. Pat. No. 5,376,538), *E. coli* MG442 (Gusyatiner et al., Genetika (in Russian), 14, 947-956 (1978)), *E. coli* VL643 and VL2055 (EP 1149911 A), and the like.

The strain TDH-6 is deficient in the thrC gene, as well as being sucrose-assimilative, and the ilvA gene has a leaky mutation. This strain also has a mutation in the rhtA gene, which imparts resistance to high concentrations of threonine or homoserine. The strain B-3996 contains the plasmid pVIC40 which was obtained by inserting a thrA*BC operon which includes a mutant thrA gene into a RSF1010-derived vector. This mutant thrA gene encodes aspartokinase homoserine dehydrogenase I which has substantially desensitized feedback inhibition by threonine. The strain B-3996 was deposited on Nov. 19, 1987 in the All-Union Scientific Center of Antibiotics (Nagatinskaya Street 3-A, 117105 Moscow, Russian Federation) under the accession number RIA 1867. The strain was also deposited in the Russian National Collection of Industrial Microorganisms (VKPM) (Russia, 117545 Moscow 1, Dorozhny proezd. 1) on Apr. 7, 1987 under the accession number B-3996.

*E. coli* VKPM B-5318 (EP 0593792B) may also be used as a parent strain to derive L-threonine-producing bacteria of the present invention. The strain B-5318 is prototrophic with regard to isoleucine, and a temperature-sensitive lambda-phage C1 repressor and PR promoter replaces the regulatory region of the threonine operon in plasmid pVIC40. The strain VKPM B-5318 was deposited in the Russian National Collection of Industrial Microorganisms (VKPM) (Russia, 117545 Moscow 1, Dorozhny proezd. 1) on May 3, 1990 under accession number of VKPM B-5318.

Preferably, the bacterium of the present invention is additionally modified to enhance expression of one or more of the following genes:

the mutant thrA gene which codes for aspartokinase homoserine dehydrogenase I resistant to feed back inhibition by threonine;

the thrB gene which codes for homoserine kinase;

the thrC gene which codes for threonine synthase;

the rhtA gene which codes for a putative transmembrane protein;

the asd gene which codes for aspartate-β-semialdehyde dehydrogenase; and the aspC gene which codes for aspartate aminotransferase (aspartate transaminase).

The sequence of the thrA gene of *Escherichia coli* which encodes aspartokinase homoserine dehydrogenase I has been elucidated (nucleotide positions 337 to 2799, GenBank accession NC_000913.2, gi: 49175990). The thrA gene is located between the thrL and thrB genes on the chromosome of *E. coli* K-12. The nucleotide sequence of the thrB gene of *Escherichia coli* which encodes homoserine kinase has been elucidated (nucleotide positions 2801 to 3733, GenBank accession NC_000913.2, gi: 49175990). The thrB gene is located between the thrA and thrC genes on the chromosome of *E. coli* K-12. The nucleotide sequence of the thrC gene of *Escherichia coli* which encodes threonine synthase has been elucidated (nucleotide positions 3734 to 5020, GenBank accession NC_000913.2, gi: 49175990). The thrC gene is located between the thrB gene and the yaaX open reading frame on the chromosome of *E. coli* K-12. All three genes function together as a single threonine operon. To enhance the expression of the threonine operon, the attenuator region which affects the transcription can be removed from the operon (WO2005/049808, WO2003/097839).

A thrA gene which has been mutated so that it encodes aspartokinase homoserine dehydrogenase I which is resistant to feedback inhibition by threonine, as well as, the thrB and thrC genes can be obtained as one operon from well-known plasmid pVIC40, which is present in the threonine producing E. coli strain VKPM B-3996. Plasmid pVIC40 is described in detail in U.S. Pat. No. 5,705,371.

The rhtA gene exists at 18 min on the E. coli chromosome close to the glnHPQ operon, which encodes components of the glutamine transport system. The rhtA gene is identical to ORF1 (ybiF gene, nucleotide positions 764 to 1651, Gen-Bank accession number AAA218541, gi:440181) and located between the pexB and ompX genes. The sequence expressing a protein encoded by the ORF1 has been designated the rhtA gene (rht: resistance to homoserine and threonine). Also, the rhtA23 mutation is an A-for-G substitution at position −1 with respect to the ATG start codon (ABSTRACTS of the 17th International Congress of Biochemistry and Molecular Biology in conjugation with Annual Meeting of the American Society for Biochemistry and Molecular Biology, San Francisco, Calif. Aug. 24-29, 1997, abstract No. 457, EP 1013765 A).

The nucleotide sequence of the asd gene of E. coli has already been elucidated (nucleotide positions 3572511 to 3571408, GenBank accession NC_000913.1, gi:16131307), and can be obtained by PCR (polymerase chain reaction; refer to White, T. J. et al., Trends Genet., 5, 185 (1989)) by utilizing primers based on the nucleotide sequence of the gene. The asd genes from other microorganisms can be obtained in a similar manne (US 2005-0124048).

Also, the nucleotide sequence of the aspC gene of E. coli has already been elucidated (nucleotide positions 983742 to 984932, GenBank accession NC_000913.1, gi:16128895), and can be obtained by PCR. The aspC genes from other microorganisms can be obtained in a similar manner (WO03/072786).

L-Cysteine-Producing Bacteria

Examples of parent strains for deriving L-cysteine-producing bacteria of the present invention include, but are not limited to, strains belonging to the genus Escherichia, such as E. coli JM15 which has been transformed with different cysE alleles coding for feedback-resistant serine acetyltransferases (U.S. Pat. No. 6,218,168, Russian patent application 2003121601), E. coli W3110 which over-expresses genes which encode proteins suitable for secreting toxic substances (U.S. Pat. No. 5,972,663), E. coli strains with decreased cysteine desulfohydrase activity (JP 11155571A2); E. coli W3110 with increased activity of a positive transcriptional regulator for the cysteine regulon encoded by the cysB gene (WO0127307A1), and the like.

L-Leucine-Producing Bacteria

Examples of parent strains for deriving L-leucine-producing bacteria of the present invention include, but are not limited to, strains belonging to the genus Escherichia, such as E. coli strains resistant to leucine (for example, the strain 57 (VKPM B-7386, U.S. Pat. No. 6,124,121)) or leucine analogs including P-2-thienylalanine, 3-hydroxyleucine, 4-azaleucine, 5,5,5-trifluoroleucine (JP 62-34397 B and JP 8-70879 A); E. coli strains obtained by the genetic engineering method described in WO96/06926; E. coli H-9068 (JP 8-70879 A), and the like.

The bacterium of the present invention may be improved by enhancing the expression of one or more genes involved in L-leucine biosynthesis. Examples of these genes include those of the leuABCD operon, which preferably include a leuA gene which has been mutated so that it encodes isopropylmalate synthase which is resistant to feedback inhibition by L-leucine (U.S. Pat. No. 6,403,342). In addition, the bacterium of the present invention may be improved by enhancing the expression of one or more genes coding for proteins which excrete L-amino acids from the bacterial cell. Examples of such genes include the b2682 and b2683 genes (ygaZH genes) (EP 1239041 A2).

L-Histidine-Producing Bacteria

Examples of parent strains for deriving L-histidine-producing bacteria of the present invention include, but are not limited to, strains belonging to the genus Escherichia, such as E. coli strain 24 (VKPM B-5945, RU2003677); E. coli strain 80 (VKPM B-7270, RU2119536); E. coli NRRL B-12116-B12121 (U.S. Pat. No. 4,388,405); E. coli H-9342 (FERM BP-6675) and H-9343 (FERM BP-6676) (U.S. Pat. No. 6,344,347); E. coli H-9341 (FERM BP-6674) (EP1085087); E. coli AI80/pFM201 (U.S. Pat. No. 6,258,554) and the like.

Examples of parent strains for deriving L-histidine-producing bacteria of the present invention also include strains in which expression of one or more genes encoding an L-histidine biosynthetic enzyme are enhanced. Examples of these L-histidine-biosynthetic enzymes include ATP phosphoribosyltransferase (hisG), phosphoribosyl AMP cyclohydrolase (hisI), phosphoribosyl-ATP pyrophosphohydrolase (hisIE), phosphoribosylformimino-5-aminoimidazole carboxamide ribotide isomerase (hisA), amidotransferase (hisH), histidinol phosphate aminotransferase (hisC), histidinol phosphatase (hisB), histidinol dehydrogenase (hisD), and so forth.

It is known that the genes encoding the L-histidine biosynthetic enzyme (hisG, hisBHAFI) are inhibited by L-histidine, and therefore an L-histidine-producing ability can also be efficiently enhanced by introducing a mutation which induces resistance to the feedback inhibition into ATP phosphoribosyltransferase (hisG) (Russian Patent Nos. 2003677 and 2119536).

Specific examples of strains having an L-histidine-producing ability include E. coli FERM-P 5038 and 5048 which have been transformed with a vector carrying a DNA encoding an L-histidine-biosynthetic enzyme (JP 56-005099 A), E. coli strains transformed with rht, a gene for an amino acid-export (EP1016710A), E. coli 80 strain imparted with sulfaguanidine, DL-1,2,4-triazole-3-alanine, and streptomycin-resistance (VKPM B-7270, Russian Patent No. 2119536), and so forth.

L-Glutamic Acid-Producing Bacteria

Examples of parent strains for deriving L-glutamic acid-producing bacteria of the present invention include, but are not limited to, strains belonging to the genus Escherichia, such as E. coli VL334thrC⁺(EP 1172433). E. coli VL334 (VKPM B-1641) is auxotrophic for L-isoleucine and L-threonine and is mutated in thrC and ilvA genes (U.S. Pat. No. 4,278,765). A wild-type allele of the thrC gene was transferred by general transduction using a bacteriophage P1 grown on the wild-type E. coli strain K12 (VKPM B-7). As a result, an L-isoleucine auxotrophic strain VL334thrC⁺ (VKPM B-8961) was obtained. This strain is able to produce L-glutamic acid.

Examples of parent strains for deriving the L-glutamic acid-producing bacteria of the present invention include, but are not limited to, strains in which expression of one or more genes encoding an L-glutamic acid biosynthetic enzyme are enhanced. Examples of the enzymes involved in L-glutamic acid biosynthesis include glutamate dehydrogenase (gdhA), glutamine synthetase (glnA), glutamate synthetase (gltAB), isocitrate dehydrogenase (icdA), aconitate hydratase (acnA, acnB), citrate synthase (gltA), phosphoenolpyruvate carboxylase (ppc), pyruvate dehydrogenase (aceEF, lpdA), pyruvate kinase (pykA, pykF), phosphoenolpyruvate synthase (ppsA), enolase (eno), phosphoglyceromutase (pgmA), phosphoglycerate kinase (pgk), glyceraldehyde-3-phophate dehydrogenase (gapA), triose phosphate isomerase (tpiA), fructose bisphosphate aldolase (fbp), phosphofructokinase (pfkA, pfkB), and glucose phosphate isomerase (pgi).

Examples of strains modified so that expression of the citrate synthetase gene, the phosphoenolpyruvate carboxylase gene, and/or the glutamate dehydrogenase gene is/are enhanced include those disclosed in EP1078989A, EP955368A, and EP952221A.

Examples of parent strains for deriving the L-glutamic acid-producing bacteria of the present invention also include strains having decreased or eliminated activity of an enzyme that catalyzes synthesis of a compound other than L-glutamic acid, and branches off from an L-glutamic acid biosynthesis pathway. Examples of such enzymes include isocitrate lyase, α-ketoglutarate dehydrogenase, phosphotransacetylase, acetate kinase, acetohydroxy acid synthase, acetolactate synthase, formate acetyltransferase, lactate dehydrogenase, and glutamate decarboxylase. Bacteria belonging to the genus *Escherichia* deficient in the α-ketoglutarate dehydrogenase activity or having a reduced α-ketoglutarate dehydrogenase activity and methods for obtaining them are described in U.S. Pat. Nos. 5,378,616 and 5,573,945.

Specifically, these strains include the following:
*E. coli* W3110sucA::Kmr
*E. coli* AJ12624 (FERM BP-3853)
*E. coli* AJ12628 (FERM BP-3854)
*E. coli* AJ12949(FERM BP-4881)

*E. coli* W3110sucA::Kmr is obtained by disrupting the α-ketoglutarate dehydrogenase gene (hereinafter referred to as "sucA gene") of *E. coli* W3110. This strain is completely deficient in α-ketoglutarate dehydrogenase.

Other examples of L-glutamic acid-producing bacterium include those which belong to the genus *Escherichia* and have resistance to an aspartic acid antimetabolite. These strains can also be deficient in the α-ketoglutarate dehydrogenase activity and include, for example, *E. coli* AJ13199 (FERM BP-5807) (U.S. Pat. No. 5,908,768), FERM P-12379, which additionally has a low L-glutamic acid decomposing ability (U.S. Pat. No. 5,393,671); AJ13138 (FERM BP-5565) (U.S. Pat. No. 6,110,714), and the like.

Examples of L-glutamic acid-producing bacteria include mutant strains belonging to the genus *Pantoea* which are deficient in α-ketoglutarate dehydrogenase activity or have a decreased α-ketoglutarate dehydrogenase activity, and can be obtained as described above. Such strains include *Pantoea ananatis* AJ13356 (U.S. Pat. No. 6,331,419). *Pantoea ananatis* AJ13356 was deposited at the National Institute of Bioscience and Human-Technology, Agency of Industrial Science and Technology, Ministry of International Trade and Industry (currently, National Institute of Advanced Industrial Science and Technology, International Patent Organism Depositary, Central 6, 1-1, Higashi 1-Chome, Tsukuba-shi, Ibaraki-ken, 305-8566, Japan) on Feb. 19, 1998 under an accession number of FERM P-16645. It was then converted to an international deposit under the provisions of Budapest Treaty on Jan. 11, 1999 and received an accession number of FERM BP-6615. *Pantoea ananatis* AJ13356 is deficient in α-ketoglutarate dehydrogenase activity as a result of disruption of the αKGDH-E1 subunit gene (sucA). The above strain was identified as *Enterobacter agglomerans* when it was isolated and deposited as the *Enterobacter agglomerans* AJ13356. However, it was recently re-classified as *Pantoea ananatis* on the basis of nucleotide sequencing of 16S rRNA and so forth. Although AJ13356 was deposited at the aforementioned depositary as *Enterobacter agglomerans*, for the purposes of this specification, they are described as *Pantoea ananatis*.

L-Phenylalanine-Producing Bacteria

Examples of parent strains for deriving L-phenylalanine-producing bacteria of the present invention include, but are not limited to, strains belonging to the genus *Escherichia*, such as *E. coli* AJ12739 (tyrA::Tn10, tyrR) (VKPM B-8197); *E. coli* HW1089 (ATCC 55371) harboring the pheA34 gene (U.S. Pat. No. 5,354,672); *E. coli* MWEC101-b (KR8903681); *E. coli* NRRL B-12141, NRRL B-12145, NRRL B-12146 and NRRL B-12147 (U.S. Pat. No. 4,407,952). Also, as a parent strain, *E. coli* K-12 [W3110 (tyrA)/pPHAB (FERM BP-3566), *E. coli* K-12 [W3110 (tyrA)/pPHAD] (FERM BP-12659), *E. coli* K-12 [W3110 (tyrA)/pPHATerm] (FERM BP-12662) and *E. coli* K-12 [W3110 (tyrA)/pBR-aroG4, pACMAB] named as AJ 12604 (FERM BP-3579) may be used (EP 488424 B1). Furthermore, L-phenylalanine producing bacteria belonging to the genus *Escherichia* which have an enhanced activity of the protein encoded by the yedA gene or the yddG gene may also be used (U.S. patent applications 2003/0148473 μl and 2003/0157667 A1).

L-Tryptophan-Producing Bacteria

Examples of parent strains for deriving the L-tryptophan-producing bacteria of the present invention include, but are not limited to, strains belonging to the genus *Escherichia*, such as *E. coli* JP4735/pMU3028 (DSM10122) and JP6015/pMU91 (DSM10123) deficient in the tryptophanyl-tRNA synthetase encoded by mutant trpS gene (U.S. Pat. No. 5,756,345); *E. coli* SV164 (pGH5) having a serA allele encoding phosphoglycerate dehydrogenase resistant to feedback inhibition by serine and a trpE allele encoding anthranilate synthase resistant to feedback inhibition by tryptophan (U.S. Pat. No. 6,180,373); *E. coli* AGX17 (pGX44) (NRRL B-12263) and AGX6(pGX50)aroP (NRRL B-12264) deficient in the enzyme tryptophanase (U.S. Pat. No. 4,371,614); *E. coli* AGX17/pGX50,pACKG4-pps in which a phosphoenolpyruvate-producing ability is enhanced (WO9708333, U.S. Pat. No. 6,319,696), and the like may be used. Furthermore, L-tryptophan producing bacteria belonging to the genus *Escherichia* which have an enhanced activity of the protein encoded by the yedA gene or the yddG gene may also be used (U.S. patent applications 2003/0148473 A1 and 2003/0157667 A1).

Examples of parent strains for deriving the L-tryptophan-producing bacteria of the present invention also include strains in which one or more activities of the enzymes selected from anthranilate synthase (trpE), phosphoglycerate dehydrogenase (serA), and tryptophan synthase (trpAB) are enhanced. The anthranilate synthase and phosphoglycerate dehydrogenase are both subject to feedback inhibition by L-tryptophan and L-serine, so a mutation which results in desensitizes the feedback inhibition may be introduced into these enzymes. Specific examples of strains having such a mutation include a *E. coli* SV164 which harbors desensitized anthranilate synthase and a strain obtained by transforming the plasmid pGH5 into *E. coli* SV164 (WO 94/08031), which contains a serA gene which has been mutated so that it encodes feedback-desensitized phosphoglycerate dehydrogenase.

Examples of parent strains for deriving the L-tryptophan-producing bacteria of the present invention also include strains transformed with the tryptophan operon which contains a gene encoding desensitized anthranilate synthase (JP 57-71397 A, JP 62-244382 A, U.S. Pat. No. 4,371,614). Moreover, L-tryptophan-producing ability may be imparted by enhancing expression of a gene which encodes tryptophan synthase, among tryptophan operons (trpBA). The tryptophan synthase consists of α and β subunits which are encoded by trpA and trpB, respectively. In addition, L-tryptophan-producing ability may be improved by enhancing expression of the isocitrate lyase-malate synthase operon (WO2005/103275).

L-Proline-Producing Bacteria

Examples of parent strains for deriving L-proline-producing bacteria of the present invention include, but are not limited to, strains belonging to the genus *Escherichia*, such as *E. coli* 702ilvA (VKPM B-8012) which is deficient in the ilvA gene and is able to produce L-proline (EP 1172433).

The bacterium of the present invention may be improved by enhancing the expression of one or more genes involved in L-proline biosynthesis. Examples of such preferred genes for L-proline producing bacteria include the proB gene coding for glutamate kinase which is desensitized to feedback inhibition by L-proline (DE Patent 3127361). In addition, the bacterium of the present invention may be improved by enhancing the expression of one or more genes coding for proteins excreting L-amino acid from the bacterial cell. Such genes are exemplified by the b2682 and b2683 genes (ygaZH genes) (EP1239041 A2).

Examples of bacteria belonging to the genus *Escherichia*, which have an activity to produce L-proline include the following *E. coli* strains: NRRL B-12403 and NRRL B-12404 (GB Patent 2075056), VKPM B-8012 (Russian patent application 2000124295), plasmid mutants described in DE Patent 3127361, plasmid mutants described by Bloom F. R. et al (The 15th Miami winter symposium, 1983, p. 34), and the like.

L-Arginine-Producing Bacteria

Examples of parent strains for deriving L-arginine-producing bacteria of the present invention include, but are not limited to, strains belonging to the genus *Escherichia*, such as *E. coli* strain 237 (VKPM B-7925) (U.S. Patent Application 2002/058315 A1) and its derivative strains harboring mutant N-acetylglutamate synthase (Russian Patent Application No. 2001112869), *E. coli* strain 382 (VKPM B-7926) (EP 1170358A1), an arginine-producing strain into which argA gene encoding N-acetylglutamate synthetase is introduced therein (EP 1170361A1), and the like.

Examples of parent strains for deriving L-arginine producing bacteria of the present invention also include strains in which expression of one or more genes encoding an L-arginine biosynthetic enzyme are enhanced. Examples of the L-arginine biosynthetic enzymes include N-acetylglutamyl phosphate reductase (argC), ornithine acetyl transferase (argJ), N-acetylglutamate kinase (argB), acetylornithine transaminase (argD), ornithine carbamoyl transferase (argF), argininosuccinic acid synthetase (argG), argininosuccinic acid lyase (argH), and carbamoyl phosphate synthetase (carAB). [YUMI1]

L-Valine-Producing Bacteria

Example of parent strains for deriving L-valine-producing bacteria of the present invention include, but are not limited to, strains which have been modified to overexpress the ilvGMEDA operon (U.S. Pat. No. 5,998,178). It is desirable to remove the region of the ilvGMEDA operon which is required for attenuation so that expression of the operon is not attenuated by the L-valine that is produced. Furthermore, the ilvA gene in the operon is desirably disrupted so that threonine deaminase activity is decreased. Examples of parent strains for deriving L-valine-producing bacteria of the present invention also include mutants of amino-acyl t-RNA synthetase (U.S. Pat. No. 5,658,766). For example, *E. coli* VL1970, which has a mutation in the ileS gene encoding isoleucine tRNA synthetase, can be used. *E. coli* VL1970 has been deposited in the Russian National Collection of Industrial Microorganisms (VKPM) (Russia, 113545 Moscow, 1 Dorozhny Proezd.) on Jun. 24, 1988 under accession number VKPM B-4411.

Furthermore, mutants requiring lipoic acid for growth and/or lacking $H^+$-ATPase can also be used as parent strains (WO96/06926).

L-Isoleucine-Producing Bacteria

Examples of parent strains for deriving L-isoleucine producing bacteria of the present invention include, but are not limited to, mutants having resistance to 6-dimethylaminopurine (JP 5-304969 A), mutants having resistance to an isoleucine analogue such as thiaisoleucine and isoleucine hydroxamate, and mutants additionally having resistance to DL-ethionine and/or arginine hydroxamate (JP 5-130882 A). In addition, recombinant strains transformed with genes encoding proteins involved in L-isoleucine biosynthesis, such as threonine deaminase and acetohydroxate synthase, can also be used as parent strains (JP 2-458 A, FR 0356739, and U.S. Pat. No. 5,998,178).

<1-2> Enhancement of the $Na^+/H^+$ Antiporter Activity

The bacterium of the present invention can be obtained by modifying a bacterium having an L-amino acid-producing ability as described above so that the $Na^+/H^+$ antiporter activity is enhanced. However, L-amino acid-producing ability may be imparted after the bacterium is modified so that the $Na^+/H^+$ antiporter activity is enhanced. The $Na^+/H^+$ antiporter activity may be enhanced by increasing the expression of a gene encoding a $Na^+/H^+$ antiporter or a gene that positively regulates the $Na^+/H^+$ antiporter activity. Gene expression can be enhanced by modifying an expression regulatory sequence such as a promoter of an endogenous gene, or enhancing expression of an exogenous gene by introducing a plasmid containing the gene, or the like. These methods may be combined.

In the present invention, the term "$Na^+/H^+$ antiporter" refers to a membrane protein involved in uptake of $H^+$ into a cytoplasm and export of $Na^+$, and the phrase "modifying so that the $Na^+/H^+$ antiporter activity is enhanced" includes when the number of $Na^+/H^+$ antiporter molecules per cell increases and when the $Na^+/H^+$ antiporter activity per molecule is increased as compared to a wild-type strain or an unmodified strain. The bacterium is modified so that $Na^+/H^+$ antiporter activity is preferably not less than 150%, more preferably not less than 200%, further more preferably not less than 300% per bacterial cell as compared to a wild-type strain or an unmodified strain. In the present invention, examples of a wild-type bacterium belonging to the Enterobacteriaceae family to be used as a control include *Escherichia coli* MG1655 strain (ATCC No. 47076), W3110 strain (ATCC No. 27325), and *Pantoea ananatis* AJ13335 strain (FERM BP-6615).

The $Na^+/H^+$ antiporter activity can be enhanced increasing expression of a gene encoding a $Na^+/H^+$ antiporter or a gene encoding a protein that positively regulates $Na^+/H^+$ antiporter activity. The increased $Na^+/H^+$ antiporter activity can be confirmed by measuring the increase in expression of the gene encoding the $Na^+/H^+$ antiporter. The increased expression can be confirmed by comparing the amount of $Na^+/H^+$ antiporter mRNA in the bacterium of the present invention with a wild-type or unmodified strain. Examples of a method of measuring the amount of expression include Northern hybridization and RT-PCR (Molecular cloning (Cold spring Harbor Laboratory Press, Cold spring Harbor (USA), 2001)). The expression may be at any level as long as the expression is increased as compared to a wild-type or unmodified strain, and for example, the amount of expression is preferably increased not less than 1.5-fold, more preferably not less than 2-fold, and more preferably not less than 3-fold as compared to a wild-type or unmodified strain. Meanwhile, enhancement of the $Na^+/H^+$ antiporter activity can also be confirmed by an increase in the amount of $Na^+/H^+$ antiporter protein as compared to a wild-type or unmodified strain, and the amount of the protein can be evaluated, for example, by Western blotting using an antibody (Molecular cloning (Cold spring Harbor Laboratory Press, Cold spring Harbor (USA), 2001)).

Examples of a gene that encodes the $Na^+/H^+$ antiporter include the nhaA gene, nhaB gene, chaA gene, and mdfA gene, and homologues thereof. In the present invention, examples of these genes from *Escherichia coli* include the nhaA gene of SEQ ID NO: 1 (nucleotide numbers 17489-18655 of GenBank Accession No. NC_000913), nhaB gene of SEQ ID NO: 3 (a complementary strand of nucleotide numbers 1232399-1233940 of GenBank Accession No. NC_000913), chaA gene of SEQ ID NO: 23 (a complementary strand of nucleotide numbers 1269972.1271072 of GenBank Accession No. NC_000913.2), and mdfA gene of SEQ ID NO: 25 (nucleotide numbers 882896.884128 of GenBank Accession No. NC_000913.2). Meanwhile, the valine at position 1 in the amino acid sequence encoded by SEQ ID NO: 1 corresponds to the codon gtg, but the codon may also be translated as methionine.

Examples of nhaA gene and nha B gene derived from other bacteria include a gene that is derived from *Yersinia pestis* strain C092 and encodes a NhaA protein having the amino acid sequence of SEQ ID NO: 7, and a gene that is derived from *Salmonella enterica* CT18 strain and encodes a NhaB protein having the amino acid sequence of SEQ ID NO: 8.

Homologues of the above-mentioned genes can be obtained by cloning, based on homologies to the above-listed genes, from coryneform bacteria such as *Corynebacterium glutamicum* and *Brevibacterium lactofermentum*, γ-Proteobacteria such as those belonging to the genus *Escherichia*, *Enterobacter*, *Klebsiella*, *Serratia*, *Erwinia*, or *Yersinia*, *Pseudomonas* bacteria such as *Pseudomonas aeruginosa*, and *Mycobacterium* bacteria such as *Mycobacterium tuberculosis*. Homologue genes may be amplified by using, for example, synthetic oligonucleotides shown in SEQ ID NOS: 9 and 10, SEQ ID NOS: 11 and 12, or SEQ ID NOS: 13 and 14 as primers. The homologies of amino acid sequences and nucleotide sequences can be determined by using the algorithm BLAST created by Karlin and Altschul (Pro. Natl. Acad. Sci. USA, 90, 5873 (1993)) or the algorithm FASTA created by Pearson (Methods Enzymol., 183, 63 (1990)). Based on the algorithm BLAST, programs called BLASTN and BLASTX have been developed (www.ncbi.nlm.nih.gov).

Examples of a gene that encodes a protein that positively regulates the $Na^+/H^+$ antiporter activity include a nhaR gene or a homologue thereof, and examples of nhaR gene from *Escherichia coli* include the nhaR gene of SEQ ID NO: 5 (nucleotide numbers 18715-19620 of GenBank Accession No. NC_000913).

Homologues of a gene encoding a $Na^+/H^+$ antiporter or of a gene encoding a protein that positively regulates $Na^+/H^+$ antiporter activity include mutant genes derived from another bacteria or a natural or artificial mutant genes, which show high structural similarity to a gene such as nhaA, nhaB, chaA, mdfA, and nhaR of *Escherichia coli* and functions to enhance the $Na^+/H^+$ antiporter activity when introduced or amplified in a host. Each of the homologue genes encoding the $Na^+/H^+$ antiporter (homologues of nhaA gene, nhaB gene, cha A gene, or mdfA gene) include genes that have homology of not less than 80%, preferably not less than 90%, more preferably not less than 95%, particularly preferably not less than 98% to each of the entire amino acid sequences of SEQ ID NO: 2, 4, 24 or 26, and encode a protein which functions as a $Na^+/H^+$ antiporter. Whether a protein functions as a $Na^+/H^+$ antiporter can be confirmed by expressing the genes in a host cell and examining the transport of $Na^+$ and $H^+$ across a membrane (Biochim Biophys Acta. 2005 Sep. 30; 1709(3): 240-50.).

Homologues of a gene encoding a protein that positively regulates the $Na^+/H^+$ antiporter activity (homologue of nhaR gene) include genes that have homology of not less than 80%, preferably not less than 90%, more preferably not less than 95%, particularly preferably not less than 98% to the entire amino acid sequence of SEQ ID NO: 6, and encode a protein capable of increasing expression amount of $Na^+/H^+$ antiporter gene, in particular, nhaA gene. The increase in the expression of the $Na^+/H^+$ antiporter gene can be confirmed by expressing the nhaR gene in a host cell and determining the transcription amount of the nhaA gene (EMBO J. 1997 Oct. 1; 16(19): 5922-9.).

Meanwhile, the nhaA gene, nhaB gene, chaA gene, and mdfA gene to be used in the present invention are not limited to wild-type genes and may be mutant or artificially modified genes that encode a protein having an amino acid sequence of SEQ ID NO: 2, 4, 24, or 26 and which may include substitution, deletion, insertion, addition of one or several amino acids at one or a plurality of positions, as long as the function of the NhaA protein, NhaB protein, ChaA protein, or MdfA protein encoded by these genes, that is, a $Na^+/H^+$ antiporter function, is maintained.

In addition, the nhaR gene to be used in the present invention is not limited to a wild-type gene and may be a mutant or an artificially modified gene that encodes a protein having an amino acid sequence of SEQ ID NO: 6 including substitution, deletion, insertion, addition of one or several amino acids at one or a plurality of positions as long as the function of NhaR protein encoded by the gene, that is, the ability to increase expression of the $Na^+/H^+$ antiporter is maintained.

In the present invention, the term "one or several" specifically means 1 to 20, preferably 1 to 10, and more preferably 1 to 5, although this determination depends on the position in the protein's tertiary structure or the types of amino acid residues in the protein. The above-mentioned substitution is preferably a conservative substitution, which may include substitutions between aromatic amino acids such as substitution among Phe, Trp and Tyr, substitution between hydrophobic amino acids such as substitution among Leu, Ile and Val, substitution between polar amino acids such as substitution between Gln and Asn, substitution between basic amino acids such as substitution among Lys, Arg and His, substitution between acidic amino acids such as substitution between Asp and Glu, substitution between hydroxyl group-containing amino acids such as substitution between Ser and Thr. Examples of conservative substitutions include substitution of Ser or Thr with ala; substitution of Gln, His or Lys with Arg; substitution of Glu, Gln, Lys, His or Asp with Asn; substitution of Asn, Glu or Gln with Asp; substitution of Ser or Ala with Cys; substitution of Asn, Glu, Lys, His, Asp or Arg with Gln; substitution of Gly, Asn, Gln, Lys or Asp with Glu; substitution of Pro with Gly; substitution of Asn, Lys, Gln, Arg or Tyr with His; substitution of Leu, Met, Val or Phe with Ile; substitution of Ile, Met, Val or Phe with Leu; substitution of Asn, Glu, Gln, His or Arg with Lys; substitution of Ile, Leu, Val or Phe with Met; substitution of Trp, Tyr, Met, Ile or Leu with Phe; substitution of Thr or Ala with Ser; substitution of Ser or Ala with Thr; substitution of Phe or Tyr with Trp; substitution of His, Phe or Trp with Tyr; and substitution of Met, Ile or Leu with Val. Meanwhile, the above-mentioned amino acid substitution, deletion, insertion, addition or inversion may be a result of a naturally-occurring mutation (mutant or variant) due to an individual difference, a difference of species of a bacterium harboring the nhaA gene, nhaB gene, chaA gene, mdfA gene, or nhaR gene.

Meanwhile, each of the nhaA gene, nhaB gene, chaA gene and mdfA gene may hybridize with a complementary strand of the nucleotide sequence of SEQ ID NO: 1, 3, 23, or 25 or a probe that can be prepared from each of the sequences under stringent conditions and encodes a protein having the $Na^+/H^+$ antiporter activity. The nhaR gene may hybridize with a complementary strand of the nucleotide sequence of SEQ ID NO: 5 or a probe that can be prepared from the sequence under stringent conditions and encodes a protein having a function to increase expression of $Na^+/H^+$ antiporter. In the present invention, the term "stringent conditions" refers to conditions where a so-called specific hybrid is formed and a non-specific hybrid is not formed. It is difficult to clearly define the conditions by numerical value, but examples thereof include conditions where DNAs having high homology, for example, at least 80%, preferably 90%, more preferably 95%, and further more preferably 98% homology hybridize with each other and DNAs having homology less than the value do not hybridize with each other; and specifically include washing typical of Southern hybridization, e.g., washing at 60° C., 1×SSC, 0.1% SDS, preferably 60° C., 0.1×SSC, 0.1% SDS, more preferably 68° C., 0.1×SSC, 0.1% SDS, once or preferably twice or three times.

Expression of the above-mentioned nhaA gene, nhaB gene, chaA gene, mdfA gene, and/or nhaR gene can be increased by, for example, increasing the copy number of the genes in a cell using a gene recombination technique. For example, a DNA fragment containing the gene is ligated to a vector that functions in the host bacterium, preferably a multi-copy vector, to thereby prepare a recombinant DNA, and the recombinant DNA is used to transform the host bacterium.

When using the nhaA gene, nhaB gene, and nhaR gene of *Escherichia coli*, the nhaA gene, nhaB gene, and nhaR gene can be obtained by PCR (polymerase chain reaction; White, T. J. et al., Trends Genet. 5, 185 (1989)) using primers based on the nucleotide sequence of SEQ ID NOS: 1, 3 or 5, for example, primers of SEQ ID NOS: 9 and 10, 11 and 12 or 13 and 14 and a chromosomal DNA of *Escherichia coli* as a template. The nhaA gene, nhaB gene, and nhaR gene from another bacterium can also be obtained by PCR from the chromosomal DNA or genomic DNA library of the bacterium using, as primers, oligonucleotides prepared based on the known sequences of the nhaA gene, nhaB gene or nhaR gene of the bacterium or of the nhaA gene, nhaB gene or nhaR gene of another kind of bacterium, or the amino acid sequence of the NhaA protein, NhaB protein, or NhaR protein; or hybridization using an oligonucleotide prepared based on the sequence as a probe. A chromosomal DNA can be prepared from a bacterium that serves as a DNA donor by the method of Saito and Miura (see H. Saito and K. Miura, Biochem. Biophys. Acta, 72, 619 (1963), Experiment Manual for Biotechnology, edited by The Society for Biotechnology, Japan, p 97-98, Baifukan Co., Ltd., 1992) or the like.

The chaA gene and mdf gene can also be obtained in the same way.

Then, a recombinant DNA is prepared by ligating the nhaA gene, nhaB gene, chaA gene, mdfA gene or nhaR gene which have been amplified by PCR to a vector DNA which is capable of functioning in the host bacterium. Examples of the vector capable of functioning in the host bacterium include vectors autonomously replicable in the host bacterium.

Examples of a vector which is autonomously replicable in *Escherichia coli* include pUC19, pUC18, pHSG299, pHSG399, pHSG398, pACYC184, (pHSG and pACYC are available from Takara Bio Inc.), RSF100 (Gene vol. 75(2), p 271-288, 1989), pBR322, pMW219, pMW119 (pMW is available form Nippon Gene Co., Ltd.), pSTV28, and pSTV29 (Takara Bio Inc.). A phage DNA vector can also be used.

To prepare ligate the gene to the above-mentioned vector, the vector is digested with a restriction enzyme corresponding to a recognition site in the terminus of a DNA fragment containing the nhaA gene, nhaB gene, chaA gene, mdfA gene or nhaR gene. Ligation is generally performed using a ligase such as T4 DNA ligase. Methods of digesting and ligating DNA, preparation of a chromosomal DNA, PCR, preparation of a plasmid DNA, transformation, design of oligonucleotides to be used as primers are methods well known to a person skilled in the art. These methods are described in Sambrook, J., Fritsch, E. F., and Maniatis, T., "Molecular Cloning A Laboratory Manual, Second Edition", Cold Sprig Harbor Laboratory Press, (1989), and the like.

The thus-prepared recombinant DNA is introduced into a bacterium in accordance with a conventional transformation method. Examples of the method include electroporation (Canadian Journal of Microbiology, 43. 197 (1997)). It is also possible to increase the DNA permeability by treating recipient cells with calcium chloride, which has been reported with *Escherichia coli* K-12 (Mandel, M. and Higa, A., J. Mol. Biol., 53, 159 (1970), and introduce a DNA into a competent cell prepared from a cell at proliferation stage, which has been reported with *Bacillus subtilis* (Duncan, C. H., Wilson, G. A and Young, F. E, Gene, 1, 153 (1977)).

The copy number of the nhaA gene, nhaB gene, chaA gene, mdfA gene, and/or nhaR gene can also be increased by introducing multiple copies of the genes into the chromosomal DNA of a bacterium. Introduction of multiple copies of the genes into the chromosomal DNA of a bacterium can be attained by homologous recombination using a target sequence present on the chromosomal DNA in multiple copies. Such a sequence present on a chromosomal DNA in multiple copies may be a repetitive DNA or an inverted repeat present on the edge of a transposing element. Alternatively, as disclosed in JP 2-109985 A, multiple copies of nhaA gene, nhaB gene, chaA gene, mdfA gene, and/or nhaR gene can be introduced into the chromosomal DNA by inserting the genes into a transposon, and transferring it so that multiple copies of the gene are integrated into the chromosomal DNA. Integration of these genes into the chromosome can be confirmed by Southern hybridization using a portion of the genes as a probe.

Furthermore, expression of the nhaA gene, nhaB gene, chaA gene, mdfA gene, and/or nhaR gene may be enhanced by, as described in WO 00/18935, substituting an expression regulatory sequence such as a promoter of the genes on a chromosomal DNA or of the genes on a plasmid with a stronger promoter, amplifying a regulator that increases expression of the genes, or deleting or attenuating a regulator that decreases expression of the genes. Examples of known strong promoters include the lac promoter, trp promoter, trc promoter, tac promoter, lambda phage PR promoter, PL promoter, and tet promoter.

The nhaR gene encodes a factor that positively regulates expression of the nhaA gene, so expression of the nhaA gene can be enhanced by amplifying expression of the nhaR gene.

Meanwhile, a promoter of nhaA gene, nhaB gene, chaA gene, mdfA gene, and/or nhaR gene can be made stronger so that expression of the genes are enhanced by introducing nucleotide substitution into it. Examples of a method of evaluating the strength of a promoter and examples of strong promoters are described in Goldstein et al. (Prokaryotic promoters in biotechnology. Biotechnol. Annu. Rev., 1995, 1, 105-128) or the like. In addition, it is known that a spacer sequence between the ribosome binding site (RBS) and translation initiation codon, especially, several nucleotides just upstream of the initiation codon, has a great influence on translation efficiency. Therefore, this sequence may be modified.

In addition, to enhance the activity of a protein encoded by the nhaA gene, nhaB gene, chaA gene, and/or mdfA gene, a mutation that increases the activity of the $Na^+/H^+$ antiporter may be introduced into the genes. Examples of such a mutation include a mutation in a promoter sequence to increase the transcription level of nhaA gene, nhaB gene, chaA gene, and/or mdfA gene, and a mutation in the coding region of these genes to increase the specific activities of the NhaA, NhaB, ChaA, or MdfA proteins. In addition, a mutation to enhance the activity of the NhaR protein that positively regulates expression of these genes may be introduced into the nhaR gene.

<2> Method of Producing L-Amino Acid

The method of producing an L-amino acid of the present invention comprises culturing the bacterium of the present invention in a medium to produce and accumulate an L-amino acid in the medium or bacterial cells, and collecting the L-amino acid from the medium or the bacterial cells.

A conventional medium to be used for fermentative production of an L-amino acid using a bacterium can be used. That is, a general medium containing a carbon source, nitrogen source, inorganic ion, and if necessary, other organic components can be used. In the present invention, examples of the carbon source include sugars such as glucose, sucrose, lactose, galactose, fructose and a starch hydrolysate; alcohols such as glycerol and sorbitol; and organic acids such as fumaric acid, citric acid and succinic acid. Examples of the nitrogen source include inorganic ammonium salts such as ammonium sulfate, ammonium chloride and ammonium phosphate; an organic nitrogen such as a soybean hydrolysate; ammonia gas; and aqueous ammonia. As organic trace nutrients, auxotrophic substances such as vitamin B1 and L-homoserine, yeast extract, and the like are preferably contained in the medium in an appropriate amount. Besides such substances, if necessary, potassium phosphate, magnesium sulfate, iron ion, manganese ion, or the like may be added in small amounts. The medium to be used in the present invention may be a natural medium or a synthetic medium as long as it contains a carbon source, nitrogen source, inorganic ion, and if necessary, other organic trace nutrients.

The culture is preferably performed under aerobic conditions for 1 to 7 days at a temperature of 24° C. to 37° C. and a pH of 5 to 9. The pH can be adjusted with an inorganic or organic acidic or alkaline substance, ammonia gas or the like. The L-amino acid can be collected from the fermentation liquid by a conventional method such as ion-exchange resin, precipitation, and other known methods. When the L-amino acid accumulates in the bacterial cells, the L-amino acid can be collected, for example, by disrupting the bacterial cells by ultrasonication or the like to release L-amino acid into the supernatant fraction, and then the bacterial cells are removed by centrifugation, followed by subjecting the resulting supernatant to an ion-exchange resin or the like.

When producing a basic amino acid, fermentation may be performed while controlling the pH of the medium during culture to 6.5-9.0 and controlling the pH of the medium after completion of the culture to 7.2-9.0, as well as controlling the pressure in the fermentation tank during fermentation so that it is positive. Alternatively, carbon dioxide or a mixed gas containing carbon dioxide may be added to the medium so that a bicarbonate ion and/or carbonate ion are present in an amount of at least 2 g/L in the culture medium during the culture period. These ions then function as counter ions against the cation of the basic amino acids, and the target basic amino acid may be collected(JP 2002-065287 A).

EXAMPLES

Hereinafter, the present invention will be described in more detail by referring to the following non-limiting examples. If not otherwise specified, reagents were purchased from Wako Pure Chemical Industries, Ltd. or Nacalai Tesque, Inc. The compositions of media used in Examples are shown below. The pH of each medium was adjusted with NaOH, KOH or HCl.

L Medium:

| | |
|---|---|
| Bacto-tryptone (Difco) | 10 g/L |
| Yeast extract (Difco) | 5 g/L |
| Sodium chloride | 10 g/L |
| pH 7.0 | |

The medium was sterilized by steam at 120° C. for 20 minutes.

L Agar Medium:

| | |
|---|---|
| L medium | 15 g/L |
| Bacto-agar | |

The medium was sterilized by steam at 120° C. for 20 minutes.

L-Lysine Production Medium for *Escherichia* Bacterium:

| | |
|---|---|
| Glucose | 40 g/L |
| Ammonium sulfate | 24 g/L |
| Potassium dihydrogen phosphate | 1.0 g/L |
| Magnesium sulfate heptahydrate | 1.0 g/L |
| Iron sulfate heptahydrate | 0.01 g/L |
| Manganese sulfate heptahydrate | 0.01 g/L |
| Yeast extract | 2.0 g/L |
| Calcium carbonate (official grade) | 50 g/L |
| | (separately sterilized) |

The medium was adjusted to pH 7.0 with potassium hydroxide and sterilized by steam at 115° C. for 10 minutes.

Glucose and $MgSO_4.7H_2O$ were separately sterilized.

Calcium carbonate (official grade) was separately sterilized by dry heat at 180° C.

Chloramphenicol (25 mg/L) was added as an antibiotic.

L-Threonine Production Medium for *Escherichia* Bacterium:

| | |
|---|---|
| Glucose | 40 g/L |
| Ammonium sulfate | 16 g/L |
| Potassium dihydrogen phosphate | 1.0 g/L |
| Magnesium sulfate heptahydrate | 1.0 g/L |
| Iron sulfate heptahydrate | 0.01 g/L |
| Manganese sulfate heptahydrate | 0.01 g/L |
| Calcium carbonate (official grade) | 30 g/L |
| | (separately sterilized) |

The medium was adjusted to pH 7.5 with potassium hydroxide and sterilized by steam at 115° C. for 10 minutes.

Glucose and MgSO$_4$.7H$_2$O were separately sterilized.

Calcium carbonate (official grade) was separately sterilized by dry heat at 180° C.

Streptomycin (100 mg/L) and chloramphenicol (25 mg/L) were added as antibiotics.

Example 1

<1> Construction of the Plasmids Used to Amplify the nhaA Gene, nhaB Gene, or nhaR Gene To investigate the effects of amplifying the nhaA gene, nhaB gene, and nhaR gene on L-lysine production, vectors for amplifying each of these genes were constructed. The entire nucleotide sequence of the genome of *Escherichia coli* (*Escherichia coli* K-12 strain) has been disclosed (Science, 277, 1453-1474 (1997)), and primers to amplify each of the genes (SEQ ID NOS: 9 and 10 for the nhaA gene, NOS: 11 and 12 for the nhaB gene, and SEQ ID NOS: 13 and 14 for the nhaR gene) were designed based on the known nucleotide sequences of these genes, which are disclosed in the publication. These primers were used to perform PCR using a chromosomal DNA of *Escherichia coli* MG1655 strain as a template. The chromosomal DNA was obtained using Bacterial Genomic DNA purification kit (Edge Bio Systems). PCR was performed using Pyrobest DNA polymerase (Takara Bio Inc.) such that a cycle of 96° C. for 20 seconds, 65° C. for 20 seconds and 72° C. for 2 minutes was repeated 25 times.

Each of the PCR products was ligated to a SmaI-digested vector pSTV28 (Takara Bio Inc.), to construct a plasmid for amplifying nhaA (pSnhaA), a plasmid for amplifying nhaB (pSnhaB), and a plasmid for amplifying nhaR (pSnhaR). Thereby, plasmids in which each of the above-mentioned genes was arranged downstream of a lac promoter in the forward direction were obtained.

Example 2

Construction of a strain in which the lysine decarboxylase-encoding genes (cadA and ldcC) are disrupted A strain which produces no lysine decarboxylase was constructed. The Lysine decarboxylases are encoded by the cadA gene (Genbank Accession No. NP_418555, SEQ ID NO: 19) and the ldcC gene (Genbank Accession No. NP_414728, SEQ ID NO: 21) (WO 96/17930). WC196 (FERM BP-5252) strain was used as the parent strain.

Disruption of the cadA gene and the ldcC gene were performed by the method developed by Datsenko and Wanner, which is called "Red-driven integration" (Proc. Natl. Acad. Sci. USA, 2000, vol. 97, No. 12, p 6640-6645) and by an excision system derived from λ phage (J. Bacteriol. 2002 September; 184(18): 5200-3. Interactions between integrase and excisionase in the phage lambda excisive nucleoprotein complex. Cho E H, Gumport R I, Gardner J F.). "Red-driven integration" makes it possible to construct a gene-disrupted strain in one step by employing a PCR product obtained by using as primers synthetic oligonucleotides designed to have a part of the targeted gene on the 5'-ends and a part of an antibiotic-resistance gene on the 3'-ends. Combining the λ phage-derived excision system permits the removal of the antibiotic-resistance gene that has been incorporated into the gene-disrupted strain (WO2005/010175).

(1) Disruption of the cadA Gene

A plasmid pMW118-attL-Cm-attR (WO2005/010175) was used as a template for PCR. The plasmid pMW 118-attL-Cm-attR was obtained by inserting attL gene and attR gene, which are attachment sites of λ phage, and the cat gene, which is an antibiotic resistance gene, into pMW 118 (Takara Bio Inc.) The genes are arranged in the following order: attL-cat-attR.

PCR was performed using, as primers, the synthetic oligonucleotides shown in SEQ ID NOS: 15 and 16, which have sequences corresponding to attL and attR on the 3'-terminals and a sequence corresponding to a part of the targeted cadA gene on the 5'-terminals.

The amplified PCR product was purified on an agarose gel and introduced into *Escherichia coli* WC196 strain by electroporation. This strain contains plasmid pKD46 which has temperature-sensitive replicability. The plasmid pKD46 (Proc. Natl. Acad. Sci. USA, 2000, vol. 97, No. 12, p 6640-6645) contains a DNA fragment of 2,154 nucleotides derived from λ phage which contains the Red recombinase-encoding genes (γ, β, and exo genes) of the λ Red homologous recombination system which is controlled by an arabinose-inducible ParaB promoter (GenBank/EMBL Accession No. J02459, nucleotide numbers 31088 to 33241). The plasmid pKD46 is necessary to integrate the PCR product into the chromosome of the WC1-96 strain.

Competent cells for electroporation were prepared as follows. That is, cells of the *Escherichia coli* WC196 strain were cultured overnight at 30° C. in LB medium containing 100 mg/L ampicillin, and then diluted 100-fold with 5 mL of SOB medium (Molecular Cloning: Laboratory manual, 2nd edition, Sambrook, J. et al., Cold Spring Harbor Laboratory Press (1989)) containing ampicillin (20 mg/L) and L-arabinose (1 mM). The diluted cells were grown with aeration at 30° C. until OD600 reached about 0.6, and then concentrated 100-fold and washed three times with 10% glycerol so that the cells were available for electroporation. The electroporation was performed with 70 μL of the competent cells and about 100 ng of the PCR product. After the electroporation, 1 mL of SOC medium (Molecular Cloning: Laboratory manual, 2nd edition, Sambrook, J. et al., Cold Spring Harbor Laboratory Press (1989)) was added to the cells, cultured at 37° C. for 2.5 hours, and then subjected to plate culture onto L-agar medium containing Cm (chloramphenicol) (25 mg/L), to thereby select Cm-resistant recombinant strains. Subsequently, to remove the plasmid pKD46, the cells were subcultured twice at 42° C. on L-agar medium containing Cm, and ampicillin resistance of the resultant colonies were examined, to thereby yield ampicillin-sensitive strains in which pKD46 was removed.

Deletion of the cadA gene in the mutant strain, which had been identified by the chloramphenicol resistance gene, was confirmed by PCR. The cadA-disrupted strain was named WC196ΔcadA::att-cat strain.

Subsequently, the above-mentioned helper plasmid pMW-intxis-ts (JP 2005-058827 A) was used to remove the att-cat gene which had been introduced into the cadA gene. The plasmid pMW-intxis-ts carries the gene encoding integrase (Int) of λ phage, and the gene encoding excisionase (Xis), and has temperature-sensitive replicability.

Competent cells of the WC196ΔcadA::att-cat strain were prepared by a conventional method, and were then transformed with the helper plasmid pMW-intxis-ts, and then subjected to plate culture at 30° C. onto L-agar medium containing 50 mg/L ampicillin, to thereby select ampicillin-resistant strains.

Subsequently, to remove the plasmid pMW-intxis-ts, the cells were subcultured twice at 42° C. on L-agar medium, and ampicillin resistance and chloramphenicol resistance of the resulting colonies were examined, to thereby yield a chloramphenicol and ampicillin-sensitive strain, in which the cadA gene was disrupted, and att-cat and pMW-intxis-ts were removed. The strain was named WC196ΔcadA.

(2) Disruption of the ldcC Gene in the WC196ΔcadA Strain

Disruption of the ldcC gene in the WC196ΔcadA strain was performed by using oligonucleotides of SEQ ID NOS: 17 and 18 as primers in the same way as described above. In this way, a cadA and ldcC-disrupted strain, WC196ΔcadAΔldcC was obtained.

Example 3

Effect of amplification of the nhaA gene, nhaB gene, and nhaR gene in an L-lysine-producing strain of *Escherichia* Bacterium Introduction of a plasmid for lysine production into the WC196ΔcadAΔldcC strain WC196ΔcadAΔldcC strain was transformed with a plasmid for lysine production, pCABD2 (WO 01/53459), which carries the dapA gene, dapB gene, and lysC gene, to thereby yield WC196ΔcadAΔldcC/pCABD2 strain (WC196LC/pCABD2).

WC196LC/pCABD2 strain was transformed with each of the plasmids prepared in Example 1: i.e., pSnhaA for amplifying nhaA; pSnhaB for amplifying nhaB; pSnhaR for amplifying nhaR; and a control plasmid pSTV28 (Takara Bio Inc.), to thereby yield chloramphenicol-resistant strains. Introduction of each of the plasmids was confirmed, and the pSnhaA-introduced strain, pSnhaB-introduced strain, pSnhaR-introduced strain, and pSTV28-introduced strain were named WC196LC/pCABD2/pSnhaA strain, WC196LC/pCABD2/pSnhaB strain, WC196LC/pCABD2/pSnhaR strain, and WC196LC/pCABD2/pSTV28 strain, respectively.

WC196LC/pCABD2/pSnhaA strain, WC196LC/pCABD2/pSnhaB strain, WC196LC/pCABD2/pSnhaR strain, and WC196LC/pCABD2/pSTV28 strain were each cultured at 37° C. in L-medium containing 50 mg/L chloramphenicol until the final OD600 reached about 0.6, and an equal volume of 40% glycerol solution was added to each culture, followed by stirring. Then, the resulting solution was dispensed in appropriate amounts and stored at −80° C. as glycerol stocks.

The glycerol stocks of the strains were thawed, and 100 μL of each stock was uniformly applied to an L-plate containing 25 mg/L chloramphenicol and 20 mg/L streptomycin and cultured at 37° C. for 24 hours. The bacterial cells which grew on the plate were suspended in 3 mL of a fermentation medium, and 1 mL of the suspension whose OD620 was about 13.5 was inoculated into 20 mL of a fermentation medium (L-lysine production medium for *Escherichia* bacterium) containing 25 mg/L chloramphenicol and 20 mg/L streptomycin in a 500 mL-Sakaguchi flask and cultured at 37° C. using a reciprocal shaker, followed by determination of the amount of L-lysine which had accumulated in the medium at 24 hours after beginning the culture. The amounts of L-lysine which accumulated in the medium were determined using Biotech Analyzer AS210 (Sakura Seiki Co, Ltd.).

Table 1 shows the amounts of L-lysine which had accumulated in the medium. In the case of WC196LC/pCABD2/pSnhaA strain, WC196LC/pCABD2/pSnhaB strain, and WC196LC/pCABD2/pSnhaR strain, the amounts of L-lysine accumulated in the medium were higher as compared to the control WC196LC/pCABD2/pSTV28 strain, which revealed that the lysine-producing ability was improved by amplifying the nhaA gene, nhaB gene, and nhaR gene.

TABLE 1

| Bacterial strain | Amount of accumulated L-lysine (g/L) 24 hours later |
|---|---|
| WC196LC/pCABD2/pSTV28 | 8.7 |
| WC196LC/pCABD2/pSnhaA | 11.8 |
| WC196LC/pCABD2/pSnhaB | 11.6 |
| WC196LC/pCABD2/pSnhaR | 14.9 |

Example 4

Effect of amplification of the nhaA Gene, nha B Gene, and nhaR Gene in an L-threonine-producing strain of *Escherichia* Bacterium B-5318 strain was used as an L-threonine-producing strain. B-5318 strain was deposited in the Russian National Collection of Industrial Bacteria (VKPM), GNII Genetika) on May 3, 1990, under accession No. VKPM B-5318. The nhaA gene, nhaB gene, and nhaR gene were each amplified in the L-threonine-producing bacterium using the plasmids prepared in Example 1.

The B-5318 strain was transformed with the plasmids prepared in Example 1: i.e., the pSnhaA for amplifying nhaA gene, pSnhaB for amplifying nhaB gene, and pSnhaR for amplifying nhaR, to thereby yield three different chloramphenicol-resistant strains. Introduction of the plasmids was confirmed, and the pSnhaA-introduced strain, pSnhaB-introduced strain, and pSnhaR-introduced strain were named B5318/pSnhaA strain, B5318/pSnhaB strain, and B5318/pSnhaR strain, respectively.

The B5318/pSnhaA strain, B5318/pSnhaB strain, and B5318/pSnhaR strain were cultured at 37° C. in an L-medium containing 25 mg/L chloramphenicol and 100 mg/L streptomycin and the control B5318 strain was cultured in an L-medium containing 100 mg/L streptomycin until the final OD600 reached about 0.6. Then, an equal volume of a 40% glycerol solution was added to the culture, followed by stirring. Then, the solution was dispensed in appropriate amounts and stored at −80° C. as glycerol stocks.

The glycerol stocks of the strains were thawed, and 100 μL of each of the plasmid-introduced strains was uniformly applied onto an L-plate containing 25 mg/L chloramphenicol and 100 mg/L streptomycin, while 100 μL of B5318 strain was uniformly applied on an L-plate containing 100 mg/L streptomycin, and they were cultured at 37° C. for 24 hours. The bacterial cells which grew on the plate were suspended in 6 mL of physiological saline, and 1 mL of each of the suspensions whose OD620 was 22.0 was inoculated into 20 mL of a fermentation medium (L-threonine production medium for *Escherichia* bacterium) containing 25 mg/L chloramphenicol and 100 mg/L streptomycin (in the case of B-5318 strain, the medium contains only 100 mg/L streptomycin) in a 500 mL-Sakaguchi flask and cultured at 37° C. for 24 hours using a reciprocal shaker. After the culture, the amounts of L-threonine which had accumulated in the medium were determined using high performance liquid chromatography.

Table 2 shows the amounts of L-threonine accumulated in the medium 6 and 24 hours after the beginning of the culture. In the case of B5318/pSnhaA strain, B5318/pSnhaB strain, and B5318/pSnhaR strain, the amounts of L-threonine which had accumulated after 6 and 24 hours were higher as compared to the control B5318 strain, which revealed that the L-threonine-producing ability was improved by amplifying nhaA gene, nhaB gene, and nhaR gene.

TABLE 2

| Bacterial strain | Amounts of accumulated L-threonine (g/L) | |
|---|---|---|
| | 6 hours later | 24 hours later |
| B5318 | 2.21 | 3.65 |
| B5318/pSnhaA | 2.55 | 3.92 |
| B5318/pSnhaB | 2.49 | 3.96 |
| B5318/pSnhaR | 2.23 | 3.73 |

INDUSTRIAL APPLICABILITY

Use of the bacterium of the present invention enables efficient fermentative production of basic amino acids such as L-lysine, L-ornithine, L-arginine, L-histidine and L-citrulline, aliphatic amino acids such as L-isoleucine, L-alanine, L-valine, L-leucine and L-glycine, hydroxy monoaminocarboxylic acids such as L-threonine and L-serine, cyclic amino acid such as L-proline, aromatic amino acids such as L-phenylalanine, L-tyrosine and L-tryptophan, sulfur-containing amino acids such as L-cysteine, L-cystine and L-methionine, or acidic amino acids such as L-glutamic acid, L-aspartic acid, L-glutamine and L-asparagine.

While the invention has been described in detail with reference to preferred embodiments thereof, it will be apparent to one skilled in the art that various changes can be made, and equivalents employed, without departing from the scope of the invention. All the cited references herein are incorporated as a part of this application by reference.

---

The invention claimed is:

1. A method of producing an L-amino acid comprising
I) culturing an L-amino acid-producing *Escherichia coli* bacterium in a medium to produce and accumulate an L-amino acid in the medium or cells of the *Escherichia coli* bacterium and
II) collecting the L-amino acid from the medium or the cells,
wherein said *Escherichia coli* bacterium has been modified so that Na$^+$/H$^+$ antiporter activity is enhanced as compared to a non-modified *Escherichia coli* bacterium by increasing expression of a gene selected from the group consisting of nhaA, nhaB, nhaR, chaA, mdfA, and combinations thereof,
wherein said L-amino acid is selected from the group consisting of L-lysine, L-threonine, and combinations thereof,
wherein the nhaA gene encodes a protein selected from the group consisting of:
(A) a protein comprising the amino acid sequence of SEQ ID NO: 2, and
(B) a protein comprising the amino acid sequence of SEQ ID NO: 2, but which includes substitution, deletion, insertion or addition of one to 10 amino acids, and has Na$^+$/H$^+$ antiporter activity,
wherein the nhaB gene encodes a protein selected from the group consisting of:

(C) a protein comprising the amino acid sequence of SEQ ID NO: 4, and
(D) a protein comprising the amino acid sequence of SEQ ID NO: 4, but which includes substitution, deletion, insertion or addition of one to 10 amino acids, and has $Na^+/H^+$ antiporter activity,
wherein the nhaR gene encodes a protein selected from the group consisting of:
(E) a protein comprising the amino acid sequence of SEQ ID NO: 6, and
(F) a protein comprising the amino acid sequence of SEQ ID NO: 6, but which includes substitution, deletion, insertion or addition of one to 10 amino acids, and is able to increase expression of an $Na^+/H^+$ antiporter,
wherein the chaA gene encodes a protein selected from the group consisting of:
(G) a protein comprising the amino acid sequence of SEQ ID NO: 24, and
(H) a protein comprising the amino acid sequence of SEQ ID NO: 24, but which includes substitution, deletion, insertion or addition of one to 10 amino acids, and has $Na^+/H^+$ antiporter activity,
wherein the mdfA gene encodes a protein selected from the group consisting of:
(I) a protein comprising the amino acid sequence of SEQ ID NO: 26, and
(J) a protein comprising the amino acid sequence of SEQ ID NO: 26, but which includes substitution, deletion, insertion or addition of one to 10 amino acids in SEQ ID NO: 26, and has $Na^+/H^+$ antiporter activity.

2. The method according to claim 1, wherein said nhaA gene comprises a DNA selected from the group consisting of:
(a) a DNA comprising the nucleotide sequence of SEQ ID NO: 1; and
(b) a DNA that hybridizes with a complementary strand of the nucleotide sequence of SEQ ID NO: 1 under stringent conditions comprising washing at 60° C., 0.1×SSC, 0.1% SDS, and wherein said DNA encodes a protein that has $Na^+/H^+$ antiporter activity.

3. The method according to claim 1, wherein said nhaB gene comprises a DNA selected from the group consisting of:
(c) a DNA comprising the nucleotide sequence shown in SEQ ID NO: 3; and
(d) a DNA that hybridizes with a complementary strand of the nucleotide sequence of SEQ ID NO: 3 under stringent conditions comprising washing at 60° C., 0.1×SSC, 0.1% SDS, and wherein said DNA encodes a protein that has $Na^+/H^+$ antiporter activity.

4. The method according to claim 1, wherein said nhaR gene comprises a DNA selected from the group consisting of:
(e) a DNA comprising the nucleotide sequence shown in SEQ ID NO: 5; and
(f) a DNA that hybridizes with a complementary strand of the nucleotide sequence of SEQ ID NO: 5 under stringent conditions comprising washing at 60° C., 0.1×SSC, 0.1% SDS, and wherein said DNA encodes a protein that is able to increase expression of an $Na^+/H^+$ antiporter.

5. The method according to claim 1, wherein said chaA gene comprises a DNA selected from the group consisting of:
(g) a DNA comprising the nucleotide sequence shown in SEQ ID NO: 23; and
(h) a DNA that hybridizes with a complementary strand of the nucleotide sequence of SEQ ID NO: 23 under stringent conditions comprising washing at 60° C., 0.1×SSC, 0.1% SDS, and wherein said DNA encodes a protein that has $Na^+/H^+$ antiporter activity.

6. The method according to claim 1, wherein said mdfA gene comprises a DNA selected from the group consisting of:
(i) a DNA comprising the nucleotide sequence shown in SEQ ID NO: 25; and
(j) a DNA that hybridizes with a complementary strand of the nucleotide sequence of SEQ ID NO: 25 under stringent conditions comprising washing at 60° C., 0.1×SSC, 0.1% SDS, and wherein said DNA encodes a protein that has $Na^+/H^+$ antiporter activity.

7. The method according to claim 1, wherein said increasing expression is obtained by a method selected from the group consisting of increasing the copy number of the gene, modifying an expression regulatory sequence of the gene, and combinations thereof.

* * * * *

SEQUENCE LISTING

```
<160> NUMBER OF SEQ ID NOS: 26

<210> SEQ ID NO 1
<211> LENGTH: 1167
<212> TYPE: DNA
<213> ORGANISM: Escherichia coli
<220> FEATURE:
<221> NAME/KEY: CDS
<222> LOCATION: (1)..(1164)

<400> SEQUENCE: 1 gtg aaa cat ctg cat cga ttc ttt agc agt gat gcc tcg gga ggc att      48
Val Lys His Leu His Arg Phe Phe Ser Ser Asp Ala Ser Gly Gly Ile
1               5                   10                  15 att ctt atc att gcc gct atc ctg gcg atg att atg gcc aac agc ggc      96
Ile Leu Ile Ile Ala Ala Ile Leu Ala Met Ile Met Ala Asn Ser Gly
                20                  25                  30 gca acc agt gga tgg tat cac gac ttt ctg gag acg ccg gtt cag ctc     144
Ala Thr Ser Gly Trp Tyr His Asp Phe Leu Glu Thr Pro Val Gln Leu
            35                  40                  45 cgg gtt ggt tca ctc gaa atc aac aaa aac atg ctg tta tgg ata aat     192
Arg Val Gly Ser Leu Glu Ile Asn Lys Asn Met Leu Leu Trp Ile Asn
        50                  55                  60 gac gcg ctg atg gcg gta ttt ttc ctg tta gtc ggt ctg gaa gtt aaa     240
Asp Ala Leu Met Ala Val Phe Phe Leu Leu Val Gly Leu Glu Val Lys
65                  70                  75                  80 cgt gaa ctg atg caa gga tcg cta gcc agc tta cgc cag gcc gca ttt     288
Arg Glu Leu Met Gln Gly Ser Leu Ala Ser Leu Arg Gln Ala Ala Phe
                85                  90                  95 cca gtt atc gcc gct att ggt ggg atg att gtg ccg gca tta ctc tat     336
Pro Val Ile Ala Ala Ile Gly Gly Met Ile Val Pro Ala Leu Leu Tyr
                100                 105                 110 ctg gct ttt aac tat gcc gat ccg att acc cgc gaa ggg tgg gcg atc     384
Leu Ala Phe Asn Tyr Ala Asp Pro Ile Thr Arg Glu Gly Trp Ala Ile
            115                 120                 125 ccg gcg gct act gac att gct ttt gca ctt ggt gta ctg gcg ctg ttg     432
Pro Ala Ala Thr Asp Ile Ala Phe Ala Leu Gly Val Leu Ala Leu Leu
        130                 135                 140 gga agt cgt gtt ccg tta gcg ctg aag atc ttt ttg atg gct ctg gct     480
Gly Ser Arg Val Pro Leu Ala Leu Lys Ile Phe Leu Met Ala Leu Ala
145                 150                 155                 160 att atc gac gat ctt ggg gcc atc att atc gca ttg ttc tac act         528
Ile Ile Asp Asp Leu Gly Ala Ile Ile Ile Ala Leu Phe Tyr Thr
                165                 170                 175
```

```
aat gac tta tcg atg gcc tct ctt ggc gtc gcg gct gta gca att gcg      576
Asn Asp Leu Ser Met Ala Ser Leu Gly Val Ala Ala Val Ala Ile Ala
        180                 185                 190 gta ctc gcg gta ttg aat ctg tgt ggt gca cgc cgc acg ggc gtc tat      624
Val Leu Ala Val Leu Asn Leu Cys Gly Ala Arg Arg Thr Gly Val Tyr
            195                 200                 205 att ctt gtt ggc gtg gtg ttg tgg act gcg gtg ttg aaa tcg ggg gtt      672
Ile Leu Val Gly Val Val Leu Trp Thr Ala Val Leu Lys Ser Gly Val
    210                 215                 220 cac gca act ctg gcg ggg gta att gtc ggc ttc ttt att cct ttg aaa      720
His Ala Thr Leu Ala Gly Val Ile Val Gly Phe Phe Ile Pro Leu Lys
225                 230                 235                 240 gag aag cat ggg cgt tct cca gcg aag cga ctg gag cat gtg ttg cac      768
Glu Lys His Gly Arg Ser Pro Ala Lys Arg Leu Glu His Val Leu His
                245                 250                 255 ccg tgg gtg gcg tat ctg att ttg ccg ctg ttt gca ttt gct aat gct      816
Pro Trp Val Ala Tyr Leu Ile Leu Pro Leu Phe Ala Phe Ala Asn Ala
            260                 265                 270 ggc gtt tca ctg caa ggc gtc acg ctg gat ggc ttg acc tcc att ctg      864
Gly Val Ser Leu Gln Gly Val Thr Leu Asp Gly Leu Thr Ser Ile Leu
    275                 280                 285 cca ttg ggg atc atc gct ggc ttg ctg att ggc aaa ccg ctg ggg att      912
Pro Leu Gly Ile Ile Ala Gly Leu Leu Ile Gly Lys Pro Leu Gly Ile
290                 295                 300 agt ctg ttc tgc tgg ttg gcg ctg cgt ttg aaa ctg gcg cat ctg cct      960
Ser Leu Phe Cys Trp Leu Ala Leu Arg Leu Lys Leu Ala His Leu Pro
305                 310                 315                 320 gag gga acg act tat cag caa att atg gtg gtg ggg atc ctg tgc ggt     1008
Glu Gly Thr Thr Tyr Gln Gln Ile Met Val Val Gly Ile Leu Cys Gly
                325                 330                 335 atc ggt ttt act atg tct atc ttt att gcc agc ctg gcc ttt ggt agc     1056
Ile Gly Phe Thr Met Ser Ile Phe Ile Ala Ser Leu Ala Phe Gly Ser
            340                 345                 350 gta gat cca gaa ctg att aac tgg gcg aaa ctc ggt atc ctg gtc ggt     1104
Val Asp Pro Glu Leu Ile Asn Trp Ala Lys Leu Gly Ile Leu Val Gly
    355                 360                 365 tct atc tct tcg gcg gta att gga tac agc tgg tta cgc gtt cgt ttg     1152
Ser Ile Ser Ser Ala Val Ile Gly Tyr Ser Trp Leu Arg Val Arg Leu
370                 375                 380 cgt cca tca gtt tga                                                  1167
Arg Pro Ser Val
385

<210> SEQ ID NO 2
<211> LENGTH: 388
<212> TYPE: PRT
<213> ORGANISM: Escherichia coli

<400> SEQUENCE: 2

Met Lys His Leu His Arg Phe Phe Ser Ser Asp Ala Ser Gly Gly Ile
1               5                   10                  15

Ile Leu Ile Ile Ala Ala Ile Leu Ala Met Ile Met Ala Asn Ser Gly
            20                  25                  30

Ala Thr Ser Gly Trp Tyr His Asp Phe Leu Glu Thr Pro Val Gln Leu
        35                  40                  45

Arg Val Gly Ser Leu Glu Ile Asn Lys Asn Met Leu Leu Trp Ile Asn
    50                  55                  60

Asp Ala Leu Met Ala Val Phe Phe Leu Leu Val Gly Leu Glu Val Lys
65                  70                  75                  80
```

-continued

```
Arg Glu Leu Met Gln Gly Ser Leu Ala Ser Leu Arg Gln Ala Ala Phe
                 85                  90                  95

Pro Val Ile Ala Ala Ile Gly Gly Met Ile Val Pro Ala Leu Leu Tyr
            100                 105                 110

Leu Ala Phe Asn Tyr Ala Asp Pro Ile Thr Arg Glu Gly Trp Ala Ile
        115                 120                 125

Pro Ala Ala Thr Asp Ile Ala Phe Ala Leu Gly Val Leu Ala Leu Leu
    130                 135                 140

Gly Ser Arg Val Pro Leu Ala Leu Lys Ile Phe Leu Met Ala Leu Ala
145                 150                 155                 160

Ile Ile Asp Asp Leu Gly Ala Ile Ile Ile Ala Leu Phe Tyr Thr
                165                 170                 175

Asn Asp Leu Ser Met Ala Ser Leu Gly Val Ala Ala Val Ala Ile Ala
            180                 185                 190

Val Leu Ala Val Leu Asn Leu Cys Gly Ala Arg Arg Thr Gly Val Tyr
        195                 200                 205

Ile Leu Val Gly Val Val Leu Trp Thr Ala Val Leu Lys Ser Gly Val
    210                 215                 220

His Ala Thr Leu Ala Gly Val Ile Val Gly Phe Phe Ile Pro Leu Lys
225                 230                 235                 240

Glu Lys His Gly Arg Ser Pro Ala Lys Arg Leu Glu His Val Leu His
                245                 250                 255

Pro Trp Val Ala Tyr Leu Ile Leu Pro Leu Phe Ala Phe Ala Asn Ala
            260                 265                 270

Gly Val Ser Leu Gln Gly Val Thr Leu Asp Gly Leu Thr Ser Ile Leu
        275                 280                 285

Pro Leu Gly Ile Ile Ala Gly Leu Leu Ile Gly Lys Pro Leu Gly Ile
    290                 295                 300

Ser Leu Phe Cys Trp Leu Ala Leu Arg Leu Lys Leu Ala His Leu Pro
305                 310                 315                 320

Glu Gly Thr Thr Tyr Gln Gln Ile Met Val Val Gly Ile Leu Cys Gly
                325                 330                 335

Ile Gly Phe Thr Met Ser Ile Phe Ile Ala Ser Leu Ala Phe Gly Ser
            340                 345                 350

Val Asp Pro Glu Leu Ile Asn Trp Ala Lys Leu Gly Ile Leu Val Gly
        355                 360                 365

Ser Ile Ser Ser Ala Val Ile Gly Tyr Ser Trp Leu Arg Val Arg Leu
    370                 375                 380

Arg Pro Ser Val
385
```

```
<210> SEQ ID NO 3
<211> LENGTH: 1542
<212> TYPE: DNA
<213> ORGANISM: Escherichia coli
<220> FEATURE:
<221> NAME/KEY: CDS
<222> LOCATION: (1)..(1539)

<400> SEQUENCE: 3 atg gag atc tcc tgg ggc cgc gcg cta tgg cgc aat ttt ttg ggc cag    48
Met Glu Ile Ser Trp Gly Arg Ala Leu Trp Arg Asn Phe Leu Gly Gln
1               5                   10                  15 tcc ccc gac tgg tac aaa ctc gcc ctc atc att ttc tta atc gta aac    96
Ser Pro Asp Trp Tyr Lys Leu Ala Leu Ile Ile Phe Leu Ile Val Asn
            20                  25                  30
```

| | | |
|---|---|---|
| ccg tta att ttc ctc atc agc cct ttc gtc gcg ggt tgg ttg ctg gta<br>Pro Leu Ile Phe Leu Ile Ser Pro Phe Val Ala Gly Trp Leu Leu Val<br>35                    40                    45 | | 144 |
| gcg gaa ttt att ttc act ctg gcg atg gcc ctg aaa tgc tac ccg ctg<br>Ala Glu Phe Ile Phe Thr Leu Ala Met Ala Leu Lys Cys Tyr Pro Leu<br>50                    55                    60 | | 192 |
| ctc ccc ggt ggt ctg ttg gct atc gaa gcg gta ttc atc ggc atg acc<br>Leu Pro Gly Gly Leu Leu Ala Ile Glu Ala Val Phe Ile Gly Met Thr<br>65                    70                    75                    80 | | 240 |
| agc gcg gaa cac gtc cgt gaa gag gtg gcg gca aat ctt gaa gtc ttg<br>Ser Ala Glu His Val Arg Glu Val Ala Ala Asn Leu Glu Val Leu<br>                    85                    90                    95 | | 288 |
| ctg tta ctg atg ttt atg gtg gcg ggt atc tat ttt atg aaa cag ctg<br>Leu Leu Leu Met Phe Met Val Ala Gly Ile Tyr Phe Met Lys Gln Leu<br>                  100                  105                  110 | | 336 |
| ttg ctg ttc ata ttt acc cgt ttg ctg tta agc att cgc tcc aaa atg<br>Leu Leu Phe Ile Phe Thr Arg Leu Leu Leu Ser Ile Arg Ser Lys Met<br>              115                  120                  125 | | 384 |
| ctg ctg tcg ctc tct ttt tgc gtg gcg gct gcg ttc ctc tcc gcg ttc<br>Leu Leu Ser Leu Ser Phe Cys Val Ala Ala Ala Phe Leu Ser Ala Phe<br>130                    135                  140 | | 432 |
| ctc gat gcc tta acc gtc gtg gcg gtg gtg atc agc gtt gca gtc ggt<br>Leu Asp Ala Leu Thr Val Val Ala Val Val Ile Ser Val Ala Val Gly<br>145                    150                  155                  160 | | 480 |
| ttt tat ggt att tat cac cgc gta gcc tct tcc cgt acc gaa gac acc<br>Phe Tyr Gly Ile Tyr His Arg Val Ala Ser Ser Arg Thr Glu Asp Thr<br>                  165                  170                  175 | | 528 |
| gac ctg caa gac gat agt cat atc gac aag cat tac aaa gtg gtt ctg<br>Asp Leu Gln Asp Asp Ser His Ile Asp Lys His Tyr Lys Val Val Leu<br>                    180                  185                  190 | | 576 |
| gaa cag ttc cgt ggc ttt ctg cgt agc ctg atg atg cat gcc ggt gtc<br>Glu Gln Phe Arg Gly Phe Leu Arg Ser Leu Met Met His Ala Gly Val<br>              195                  200                  205 | | 624 |
| ggc acc gca tta ggc ggc gta atg acc atg gtg ggc gaa cca cag aac<br>Gly Thr Ala Leu Gly Gly Val Met Thr Met Val Gly Glu Pro Gln Asn<br>210                    215                  220 | | 672 |
| ctg atc atc gct aaa gcg gct ggc tgg cat ttt ggc gat ttc ttc ctg<br>Leu Ile Ile Ala Lys Ala Ala Gly Trp His Phe Gly Asp Phe Phe Leu<br>225                    230                  235                  240 | | 720 |
| cgc atg tcg ccg gtg acc gtt ccg gtt ctg att tgt ggc ctg tta acc<br>Arg Met Ser Pro Val Thr Val Pro Val Leu Ile Cys Gly Leu Leu Thr<br>                  245                  250                  255 | | 768 |
| tgc ctg ctg gta gag aag ctg cgt tgg ttt ggc tac ggt gaa acg ctg<br>Cys Leu Leu Val Glu Lys Leu Arg Trp Phe Gly Tyr Gly Glu Thr Leu<br>              260                  265                  270 | | 816 |
| ccg gag aaa gtc cgc gaa gtg ttg caa cag ttt gac gat caa agc cgc<br>Pro Glu Lys Val Arg Glu Val Leu Gln Gln Phe Asp Asp Gln Ser Arg<br>275                    280                  285 | | 864 |
| cac cag cgt acc cgt cag gat aaa atc cgt ctg att gtc cag gcg att<br>His Gln Arg Thr Arg Gln Asp Lys Ile Arg Leu Ile Val Gln Ala Ile<br>290                    295                  300 | | 912 |
| att ggc gtc tgg ctg gtg act gcg ctg gcg ttg cat ctg gcg gaa gtt<br>Ile Gly Val Trp Leu Val Thr Ala Leu Ala Leu His Leu Ala Glu Val<br>305                    310                  315                  320 | | 960 |
| ggc ttg att ggt ttg tca gtc att att ctg gca aca tca ttg acc ggt<br>Gly Leu Ile Gly Leu Ser Val Ile Ile Leu Ala Thr Ser Leu Thr Gly<br>                  325                  330                  335 | | 1008 |
| gtc acc gat gag cat gct atc ggt aaa gcc ttc acc gaa tct ctg cca<br>Val Thr Asp Glu His Ala Ile Gly Lys Ala Phe Thr Glu Ser Leu Pro<br>340                    345                  350 | | 1056 |

```
ttc acc gca ctg ttg acg gtg ttt ttc tcg gta gtc gcg gtg att atc    1104
Phe Thr Ala Leu Leu Thr Val Phe Phe Ser Val Val Ala Val Ile Ile
            355                 360                 365 gac caa caa ctg ttt tcg cca att att cag ttt gtg ttg cag gca tcg    1152
Asp Gln Gln Leu Phe Ser Pro Ile Ile Gln Phe Val Leu Gln Ala Ser
370                 375                 380 gaa cat gct cag ctg tcg ctg ttc tat att ttc aac ggt ctg ctg tca    1200
Glu His Ala Gln Leu Ser Leu Phe Tyr Ile Phe Asn Gly Leu Leu Ser
385                 390                 395                 400 tcc att tcg gat aac gtc ttc gtg ggg acg att tat atc aac gaa gcg    1248
Ser Ile Ser Asp Asn Val Phe Val Gly Thr Ile Tyr Ile Asn Glu Ala
                405                 410                 415 aaa gcg gca atg gaa agt ggc gct atc acg ttg aag caa tac gag ctg    1296
Lys Ala Ala Met Glu Ser Gly Ala Ile Thr Leu Lys Gln Tyr Glu Leu
            420                 425                 430 ctg gcg gtc gcc att aat acc ggt acc aat ctg ccc tcc gtc gct acg    1344
Leu Ala Val Ala Ile Asn Thr Gly Thr Asn Leu Pro Ser Val Ala Thr
            435                 440                 445 ccg aac ggt cag gct gcg ttc ctg ttc ctg acc tct gca ctc gcg        1392
Pro Asn Gly Gln Ala Ala Phe Leu Phe Leu Thr Ser Ala Leu Ala
450                 455                 460 cca ttg att cgc ctc tct tat ggc cgc atg gtg tgg atg gcc ctg cct    1440
Pro Leu Ile Arg Leu Ser Tyr Gly Arg Met Val Trp Met Ala Leu Pro
465                 470                 475                 480 tac acc ctc gtc ctg aca ctc gtc ggc ttg ctc tgc gtc gag ttt acg    1488
Tyr Thr Leu Val Leu Thr Leu Val Gly Leu Leu Cys Val Glu Phe Thr
                485                 490                 495 ctt gcc cct gta acc gaa tgg ttt atg caa atg ggc tgg ata gca acg    1536
Leu Ala Pro Val Thr Glu Trp Phe Met Gln Met Gly Trp Ile Ala Thr
            500                 505                 510 ctt tga                                                            1542
Leu

<210> SEQ ID NO 4
<211> LENGTH: 513
<212> TYPE: PRT
<213> ORGANISM: Escherichia coli

<400> SEQUENCE: 4

Met Glu Ile Ser Trp Gly Arg Ala Leu Trp Arg Asn Phe Leu Gly Gln
1               5                   10                  15

Ser Pro Asp Trp Tyr Lys Leu Ala Leu Ile Ile Phe Leu Ile Val Asn
                20                  25                  30

Pro Leu Ile Phe Leu Ile Ser Pro Phe Val Ala Gly Trp Leu Leu Val
            35                  40                  45

Ala Glu Phe Ile Phe Thr Leu Ala Met Ala Leu Lys Cys Tyr Pro Leu
        50                  55                  60

Leu Pro Gly Gly Leu Leu Ala Ile Glu Ala Val Phe Ile Gly Met Thr
65                  70                  75                  80

Ser Ala Glu His Val Arg Glu Val Ala Ala Asn Leu Glu Val Leu
                85                  90                  95

Leu Leu Leu Met Phe Met Val Ala Gly Ile Tyr Phe Met Lys Gln Leu
            100                 105                 110

Leu Leu Phe Ile Phe Thr Arg Leu Leu Leu Ser Ile Arg Ser Lys Met
        115                 120                 125

Leu Leu Ser Leu Ser Phe Cys Val Ala Ala Phe Leu Ser Ala Phe
    130                 135                 140

Leu Asp Ala Leu Thr Val Val Ala Val Val Ile Ser Val Ala Val Gly
145                 150                 155                 160
```

```
Phe Tyr Gly Ile Tyr His Arg Val Ala Ser Arg Thr Glu Asp Thr
                165                 170                 175

Asp Leu Gln Asp Asp Ser His Ile Asp Lys His Tyr Lys Val Val Leu
            180                 185                 190

Glu Gln Phe Arg Gly Phe Leu Arg Ser Leu Met Met His Ala Gly Val
            195                 200                 205

Gly Thr Ala Leu Gly Gly Val Met Thr Met Val Gly Glu Pro Gln Asn
    210                 215                 220

Leu Ile Ile Ala Lys Ala Gly Trp His Phe Gly Asp Phe Phe Leu
225                 230                 235                 240

Arg Met Ser Pro Val Thr Val Pro Val Leu Ile Cys Gly Leu Leu Thr
                245                 250                 255

Cys Leu Leu Val Glu Lys Leu Arg Trp Phe Gly Tyr Gly Glu Thr Leu
                260                 265                 270

Pro Glu Lys Val Arg Glu Val Leu Gln Gln Phe Asp Asp Gln Ser Arg
            275                 280                 285

His Gln Arg Thr Arg Gln Asp Lys Ile Arg Leu Ile Val Gln Ala Ile
    290                 295                 300

Ile Gly Val Trp Leu Val Thr Ala Leu Ala Leu His Leu Ala Glu Val
305                 310                 315                 320

Gly Leu Ile Gly Leu Ser Val Ile Ile Leu Ala Thr Ser Leu Thr Gly
                325                 330                 335

Val Thr Asp Glu His Ala Ile Gly Lys Ala Phe Thr Glu Ser Leu Pro
            340                 345                 350

Phe Thr Ala Leu Leu Thr Val Phe Phe Ser Val Ala Val Ile Ile
            355                 360                 365

Asp Gln Gln Leu Phe Ser Pro Ile Ile Gln Phe Val Leu Gln Ala Ser
    370                 375                 380

Glu His Ala Gln Leu Ser Leu Phe Tyr Ile Phe Asn Gly Leu Leu Ser
385                 390                 395                 400

Ser Ile Ser Asp Asn Val Phe Val Gly Thr Ile Tyr Ile Asn Glu Ala
                405                 410                 415

Lys Ala Ala Met Glu Ser Gly Ala Ile Thr Leu Lys Gln Tyr Glu Leu
            420                 425                 430

Leu Ala Val Ala Ile Asn Thr Gly Thr Asn Leu Pro Ser Val Ala Thr
    435                 440                 445

Pro Asn Gly Gln Ala Ala Phe Leu Phe Leu Leu Thr Ser Ala Leu Ala
    450                 455                 460

Pro Leu Ile Arg Leu Ser Tyr Gly Arg Met Val Trp Met Ala Leu Pro
465                 470                 475                 480

Tyr Thr Leu Val Leu Thr Leu Val Gly Leu Leu Cys Val Glu Phe Thr
                485                 490                 495

Leu Ala Pro Val Thr Glu Trp Phe Met Gln Met Gly Trp Ile Ala Thr
            500                 505                 510

Leu

<210> SEQ ID NO 5
<211> LENGTH: 906
<212> TYPE: DNA
<213> ORGANISM: Escherichia coli
<220> FEATURE:
<221> NAME/KEY: CDS
<222> LOCATION: (1)..(903)
```

```
<400> SEQUENCE: 5 atg agc atg tct cat atc aat tac aac cac ttg tat tac ttc tgg cat         48
Met Ser Met Ser His Ile Asn Tyr Asn His Leu Tyr Tyr Phe Trp His
1               5                   10                  15 gtc tat aaa gaa ggt tcc gtg gtt ggc gca gcg gag gcg ctt tat tta         96
Val Tyr Lys Glu Gly Ser Val Val Gly Ala Ala Glu Ala Leu Tyr Leu
            20                  25                  30 act cca caa acc att acc gga cag att cga gcg ctg gaa gag cgc ctg        144
Thr Pro Gln Thr Ile Thr Gly Gln Ile Arg Ala Leu Glu Glu Arg Leu
        35                  40                  45 caa ggc aaa tta ttt aaa cgc aag gga cgt ggt ctc gaa ccc agc gag        192
Gln Gly Lys Leu Phe Lys Arg Lys Gly Arg Gly Leu Glu Pro Ser Glu
50                  55                  60 ctg gga gaa ctg gtc tat cgc tat gcc gat aaa atg ttc acc tta agc        240
Leu Gly Glu Leu Val Tyr Arg Tyr Ala Asp Lys Met Phe Thr Leu Ser
65                  70                  75                  80 cag gaa atg ctg gat att gtg aac tat cgc aaa gaa tcc aat tta ttg        288
Gln Glu Met Leu Asp Ile Val Asn Tyr Arg Lys Glu Ser Asn Leu Leu
                85                  90                  95 ttt gac gtt ggc gtg gct gat gca ctt tcc aaa cgc ctg gtc agt agc        336
Phe Asp Val Gly Val Ala Asp Ala Leu Ser Lys Arg Leu Val Ser Ser
            100                 105                 110 gta ctt aac gcc gca gtg gta gaa ggc gag ccc att cat ctt cgc tgc        384
Val Leu Asn Ala Ala Val Val Glu Gly Glu Pro Ile His Leu Arg Cys
        115                 120                 125 ttc gaa tcc acc cac gaa atg ctg ctg gag caa tta agt cag cat aaa        432
Phe Glu Ser Thr His Glu Met Leu Leu Glu Gln Leu Ser Gln His Lys
    130                 135                 140 ctg gat atg atc att tct gac tgt ccg ata gac tct acg cag cag gaa        480
Leu Asp Met Ile Ile Ser Asp Cys Pro Ile Asp Ser Thr Gln Gln Glu
145                 150                 155                 160 ggc ctg ttc tcc gtg aga att ggc gaa tgt ggc gtg agt ttc tgg tgt        528
Gly Leu Phe Ser Val Arg Ile Gly Glu Cys Gly Val Ser Phe Trp Cys
                165                 170                 175 aca aat cca cca cca gaa aaa ccg ttc ccg gct tgt ctg gaa gaa cgg        576
Thr Asn Pro Pro Pro Glu Lys Pro Phe Pro Ala Cys Leu Glu Glu Arg
            180                 185                 190 cga ctt ttg att cct ggg cga cgt tca atg tta ggg cgc aaa ttg ctt        624
Arg Leu Leu Ile Pro Gly Arg Arg Ser Met Leu Gly Arg Lys Leu Leu
        195                 200                 205 aac tgg ttt aac tcc cag gga tta aac gta gaa atc ctc ggc gag ttt        672
Asn Trp Phe Asn Ser Gln Gly Leu Asn Val Glu Ile Leu Gly Glu Phe
    210                 215                 220 gat gat gcc gct ttg atg aaa gct ttt ggt gcg atg cac aat gca atc        720
Asp Asp Ala Ala Leu Met Lys Ala Phe Gly Ala Met His Asn Ala Ile
225                 230                 235                 240 ttc gtt gcc cca acg ctt tat gca tat gac ttt tat gcc gat aaa act        768
Phe Val Ala Pro Thr Leu Tyr Ala Tyr Asp Phe Tyr Ala Asp Lys Thr
                245                 250                 255 gtc gta gaa att ggt cgc gtc gag aat gtg atg gaa gag tac cat gct        816
Val Val Glu Ile Gly Arg Val Glu Asn Val Met Glu Glu Tyr His Ala
            260                 265                 270 att ttt gct gag cgg atg att cag cac ccg gcg gta cag cga atc tgc        864
Ile Phe Ala Glu Arg Met Ile Gln His Pro Ala Val Gln Arg Ile Cys
        275                 280                 285 aat acg gat tat tct gcg ctt ttt agt cca gcg gtg cgt taa              906
Asn Thr Asp Tyr Ser Ala Leu Phe Ser Pro Ala Val Arg
    290                 295                 300
```

<210> SEQ ID NO 6
<211> LENGTH: 301
<212> TYPE: PRT
<213> ORGANISM: Escherichia coli

<400> SEQUENCE: 6

```
Met Ser Met Ser His Ile Asn Tyr Asn His Leu Tyr Tyr Phe Trp His
1               5                   10                  15

Val Tyr Lys Glu Gly Ser Val Val Gly Ala Ala Glu Ala Leu Tyr Leu
            20                  25                  30

Thr Pro Gln Thr Ile Thr Gly Gln Ile Arg Ala Leu Glu Glu Arg Leu
        35                  40                  45

Gln Gly Lys Leu Phe Lys Arg Lys Gly Arg Gly Leu Glu Pro Ser Glu
    50                  55                  60

Leu Gly Glu Leu Val Tyr Arg Tyr Ala Asp Lys Met Phe Thr Leu Ser
65                  70                  75                  80

Gln Glu Met Leu Asp Ile Val Asn Tyr Arg Lys Glu Ser Asn Leu Leu
                85                  90                  95

Phe Asp Val Gly Val Ala Asp Ala Leu Ser Lys Arg Leu Val Ser Ser
            100                 105                 110

Val Leu Asn Ala Ala Val Val Glu Gly Glu Pro Ile His Leu Arg Cys
        115                 120                 125

Phe Glu Ser Thr His Glu Met Leu Leu Glu Gln Leu Ser Gln His Lys
    130                 135                 140

Leu Asp Met Ile Ile Ser Asp Cys Pro Ile Asp Ser Thr Gln Gln Glu
145                 150                 155                 160

Gly Leu Phe Ser Val Arg Ile Gly Glu Cys Gly Val Ser Phe Trp Cys
                165                 170                 175

Thr Asn Pro Pro Pro Glu Lys Pro Phe Pro Ala Cys Leu Glu Glu Arg
            180                 185                 190

Arg Leu Leu Ile Pro Gly Arg Arg Ser Met Leu Gly Arg Lys Leu Leu
        195                 200                 205

Asn Trp Phe Asn Ser Gln Gly Leu Asn Val Glu Ile Leu Gly Glu Phe
    210                 215                 220

Asp Asp Ala Ala Leu Met Lys Ala Phe Gly Ala Met His Asn Ala Ile
225                 230                 235                 240

Phe Val Ala Pro Thr Leu Tyr Ala Tyr Asp Phe Tyr Ala Asp Lys Thr
                245                 250                 255

Val Val Glu Ile Gly Arg Val Glu Asn Val Met Glu Glu Tyr His Ala
            260                 265                 270

Ile Phe Ala Glu Arg Met Ile Gln His Pro Ala Val Gln Arg Ile Cys
        275                 280                 285

Asn Thr Asp Tyr Ser Ala Leu Phe Ser Pro Ala Val Arg
    290                 295                 300
```

<210> SEQ ID NO 7
<211> LENGTH: 394
<212> TYPE: PRT
<213> ORGANISM: Yersinia pestis

<400> SEQUENCE: 7

```
Met Thr Asn Ile Ile Arg Gln Phe Leu Arg Gln Glu Ala Ala Gly Gly
1               5                   10                  15

Leu Ile Leu Ile Ile Ala Ala Ala Ile Ala Leu Leu Met Ala Asn Ser
            20                  25                  30

Ala Leu Gln Gly Val Tyr Gln Ser Phe Leu Asp Ile Pro Val Ser Ile
        35                  40                  45
```

Lys Ile Ala Ser Leu Asp Ile Ser Lys Pro Leu Leu Leu Trp Ile Asn
 50                  55                  60

Asp Gly Leu Met Ala Val Phe Phe Leu Met Ile Gly Leu Glu Val Lys
 65                  70                  75                  80

Arg Glu Leu Met Glu Gly Ser Leu Ala Gly Arg Asp Lys Ala Val Phe
                 85                  90                  95

Pro Ala Ile Ala Ala Leu Gly Gly Met Leu Ala Pro Ala Leu Ile Tyr
            100                 105                 110

Leu Leu Phe Asn Gly Ala Asp Glu Val Thr Arg Gln Gly Trp Ala Ile
        115                 120                 125

Pro Ala Ala Thr Asp Ile Ala Phe Ala Leu Gly Val Met Ala Leu Leu
    130                 135                 140

Gly Asn Arg Val Pro Thr Gly Leu Lys Val Phe Leu Leu Ala Leu Ala
145                 150                 155                 160

Ile Ile Asp Asp Leu Gly Val Ile Ile Ile Ala Leu Phe Tyr Thr
                165                 170                 175

Gln Gln Val Ser Leu Gln Ser Leu Gly Ile Ala Ala Ala Ile Ala
            180                 185                 190

Leu Leu Ala Tyr Met Asn Trp Arg Gly Val Gly Lys Thr Ser Ala Tyr
        195                 200                 205

Leu Leu Val Gly Leu Val Leu Trp Val Cys Ile Leu Lys Ser Gly Val
    210                 215                 220

His Ala Thr Leu Ala Gly Val Ile Val Gly Phe Met Ile Pro Leu His
225                 230                 235                 240

Thr Gln Asp Gln Arg Ser Pro Ser Glu Ser Leu Glu His Gly Leu His
                245                 250                 255

Pro Trp Val Ala Tyr Leu Ile Leu Pro Leu Phe Ala Phe Ala Asn Ala
            260                 265                 270

Gly Val Ser Leu Gln Gly Val Ser Leu Ser Gly Leu Thr Ser Leu Leu
        275                 280                 285

Pro Met Gly Ile Ala Thr Gly Leu Phe Ile Gly Lys Pro Leu Gly Ile
    290                 295                 300

Phe Thr Phe Ser Trp Leu Ala Val Lys Leu Gly Ile Ala Lys Leu Pro
305                 310                 315                 320

Asp Ala Ile Asn Phe Lys Gln Ile Phe Ala Val Ser Val Leu Cys Gly
                325                 330                 335

Ile Gly Phe Thr Met Ser Ile Phe Ile Ala Ser Leu Ala Phe Glu Gly
            340                 345                 350

Thr Asp Ile Ala Leu Thr Thr Tyr Ser Lys Leu Gly Ile Leu Leu Gly
        355                 360                 365

Ser Thr Thr Ala Ala Val Val Gly Tyr Ser Leu Leu Arg Leu Val Leu
    370                 375                 380

Pro Ala Arg Arg Lys Ala Val Asn Val Arg
385                 390

<210> SEQ ID NO 8
<211> LENGTH: 514
<212> TYPE: PRT
<213> ORGANISM: Salmonella enterica

<400> SEQUENCE: 8

Met Glu Ile Ser Trp Gly Arg Ala Met Trp Arg Asn Phe Leu Gly Gln
1               5                   10                  15

Ser Pro Asp Trp Tyr Lys Leu Ala Leu Leu Val Phe Leu Ile Val Asn
            20                  25                  30

-continued

Pro Phe Ile Phe Leu Ala Asn Pro Phe Val Ala Gly Trp Leu Leu Val
    35                  40                  45

Ala Glu Phe Ile Phe Thr Leu Ala Met Ala Leu Lys Cys Tyr Pro Leu
 50                  55                  60

Leu Pro Gly Gly Leu Leu Ala Ile Glu Ala Val Ile Ile Gly Met Thr
 65                  70                  75                  80

Ser Ala Ala His Val Arg Glu Glu Val Ala Ala Asn Leu Glu Val Leu
                 85                  90                  95

Leu Leu Leu Met Phe Met Val Ala Gly Ile Tyr Phe Met Lys Gln Leu
            100                 105                 110

Leu Leu Phe Ile Phe Thr Arg Leu Leu Leu Ser Ile Arg Ser Lys Met
            115                 120                 125

Val Leu Ser Leu Ala Phe Cys Val Ala Ala Phe Leu Ser Ala Phe
130                 135                 140

Leu Asp Ala Leu Thr Val Val Ala Val Val Ile Ser Val Ala Val Gly
145                 150                 155                 160

Phe Tyr Gly Ile Tyr His Arg Val Ala Ser Arg Gly Glu Glu Asn
                165                 170                 175

Asp Met Leu Asp Asp Ser His Ile Asp Pro His Tyr Lys Thr Val Leu
            180                 185                 190

Glu Gln Phe Arg Gly Phe Leu Arg Ser Leu Met Met His Ala Gly Val
            195                 200                 205

Gly Thr Ala Leu Gly Gly Val Met Thr Met Val Gly Glu Pro Gln Asn
210                 215                 220

Leu Ile Ile Ala Lys Ala Ala Gly Trp His Phe Gly Asp Phe Leu
225                 230                 235                 240

Arg Met Ser Pro Val Thr Val Pro Val Leu Val Cys Gly Leu Leu Thr
                245                 250                 255

Cys Met Leu Val Glu Lys Met Arg Trp Phe Gly Tyr Gly Glu Thr Leu
            260                 265                 270

Pro Glu Lys Val Arg Asp Val Leu Gln Gln Phe Asp Asp Gln Ser Arg
            275                 280                 285

Lys Lys Arg Thr Arg Gln Asp Lys Ile Lys Leu Ile Val Gln Ala Val
290                 295                 300

Ile Gly Val Trp Leu Val Thr Ala Leu Ala Leu His Leu Ala Glu Val
305                 310                 315                 320

Gly Leu Ile Gly Leu Ser Val Ile Leu Ala Thr Ala Leu Thr Gly
                325                 330                 335

Val Thr Asp Glu His Ala Ile Gly Lys Ala Phe Thr Glu Ser Leu Pro
            340                 345                 350

Phe Thr Ala Leu Leu Thr Val Phe Phe Ser Ile Val Ala Val Ile Ile
            355                 360                 365

Asp Gln His Leu Phe Ala Pro Ile Ile Gln Phe Val Leu Gln Ala Ser
370                 375                 380

Glu His Ala Gln Leu Thr Leu Phe Tyr Leu Phe Asn Gly Leu Leu Ser
385                 390                 395                 400

Ser Ile Ser Asp Asn Val Phe Val Gly Thr Ile Tyr Ile Asn Glu Ala
                405                 410                 415

Lys Ala Ala Met Glu Asn Gly Ala Ile Ser Leu Lys Gln Phe Glu Leu
            420                 425                 430

Leu Ala Val Ala Ile Asn Thr Gly Thr Asn Leu Pro Ser Val Ala Thr
            435                 440                 445

Pro Asn Gly Gln Ala Ala Phe Leu Phe Leu Leu Thr Ser Ala Leu Ala
450                 455                 460

```
Pro Leu Ile Arg Leu Ser Tyr Gly Arg Met Val Trp Met Ala Leu Pro
465                 470                 475                 480

Tyr Thr Ile Val Leu Thr Leu Ile Gly Leu Leu Cys Val Glu Phe Thr
                485                 490                 495

Leu Ala Pro Ala Thr Glu Trp Met Thr Gln Ala Gly Trp Leu Ala Thr
            500                 505                 510

Leu Ser
```

<210> SEQ ID NO 9
<211> LENGTH: 25
<212> TYPE: DNA
<213> ORGANISM: Artificial Sequence
<220> FEATURE:
<223> OTHER INFORMATION: 5'-primer for nhaA

<400> SEQUENCE: 9
gctattatat cgctctcttt aaccc                                         25

<210> SEQ ID NO 10
<211> LENGTH: 22
<212> TYPE: DNA
<213> ORGANISM: Artificial Sequence
<220> FEATURE:
<223> OTHER INFORMATION: 3'-primer for nhaA

<400> SEQUENCE: 10
atgagacatg ctcatttctc tc                                            22

<210> SEQ ID NO 11
<211> LENGTH: 21
<212> TYPE: DNA
<213> ORGANISM: Artificial Sequence
<220> FEATURE:
<223> OTHER INFORMATION: 5'-primer for nhaB

<400> SEQUENCE: 11
taatgtactc ttccgcgaaa c                                             21

<210> SEQ ID NO 12
<211> LENGTH: 21
<212> TYPE: DNA
<213> ORGANISM: Artificial Sequence
<220> FEATURE:
<223> OTHER INFORMATION: 3'-primer for nhaB

<400> SEQUENCE: 12
gcaaggtttc agtaacatca c                                             21

<210> SEQ ID NO 13
<211> LENGTH: 35
<212> TYPE: DNA
<213> ORGANISM: Artificial Sequence
<220> FEATURE:
<223> OTHER INFORMATION: 5'-primer for nhaR

<400> SEQUENCE: 13
gcggtatcgg ttttactatg tctatcttta ttgcc                              35

<210> SEQ ID NO 14
<211> LENGTH: 30
<212> TYPE: DNA
<213> ORGANISM: Artificial Sequence
<220> FEATURE:
<223> OTHER INFORMATION: 3'-primer for nhaR -continued

```
<210> SEQ ID NO 14
```

<400> SEQUENCE: 14
catgacaaag tcatcgggca ttatctgaac                                         30

```
<210> SEQ ID NO 15
<211> LENGTH: 54
<212> TYPE: DNA
<213> ORGANISM: Artificial Sequence
<220> FEATURE:
<223> OTHER INFORMATION: 5'-primer for cadA
```

<400> SEQUENCE: 15
tttgctttct tctttcaata ccttaacggt atagcgtgaa gcctgctttt ttat             54

```
<210> SEQ ID NO 16
<211> LENGTH: 54
<212> TYPE: DNA
<213> ORGANISM: Artificial Sequence
<220> FEATURE:
<223> OTHER INFORMATION: 3'-primer for cadA
```

<400> SEQUENCE: 16
agatatgact atgaacgtta ttgcaatatt gaatcacgct caagttagta taaa             54

```
<210> SEQ ID NO 17
<211> LENGTH: 54
<212> TYPE: DNA
<213> ORGANISM: Artificial Sequence
<220> FEATURE:
<223> OTHER INFORMATION: 5'-primer for ldc
```

<400> SEQUENCE: 17
ggaggaacac atgaacatca ttgccattat gggacctgaa gcctgctttt ttat             54

```
<210> SEQ ID NO 18
<211> LENGTH: 53
<212> TYPE: DNA
<213> ORGANISM: Artificial Sequence
<220> FEATURE:
<223> OTHER INFORMATION: 3'-primer for ldc
```

<400> SEQUENCE: 18
cgccattttt aggactcgta cgcggtaaac gccgtccgtc aagttagtat aaa              53

```
<210> SEQ ID NO 19
<211> LENGTH: 2148
<212> TYPE: DNA
<213> ORGANISM: Escherichia coli
<220> FEATURE:
<221> NAME/KEY: CDS
<222> LOCATION: (1)..(2145)
```

<400> SEQUENCE: 19

| atg | aac | gtt | att | gca | ata | ttg | aat | cac | atg | ggg | gtt | tat | ttt | aaa | gaa | 48 |
|---|---|---|---|---|---|---|---|---|---|---|---|---|---|---|---|---|
| Met | Asn | Val | Ile | Ala | Ile | Leu | Asn | His | Met | Gly | Val | Tyr | Phe | Lys | Glu | |
| 1 | | | | 5 | | | | | 10 | | | | | 15 | | |

| gaa | ccc | atc | cgt | gaa | ctt | cat | cgc | gcg | ctt | gaa | cgt | ctg | aac | ttc | cag | 96 |
|---|---|---|---|---|---|---|---|---|---|---|---|---|---|---|---|---|
| Glu | Pro | Ile | Arg | Glu | Leu | His | Arg | Ala | Leu | Glu | Arg | Leu | Asn | Phe | Gln | |
| | | | 20 | | | | | 25 | | | | | 30 | | | |

| att | gtt | tac | ccg | aac | gac | cgt | gac | gac | tta | tta | aaa | ctg | atc | gaa | aac | 144 |
|---|---|---|---|---|---|---|---|---|---|---|---|---|---|---|---|---|
| Ile | Val | Tyr | Pro | Asn | Asp | Arg | Asp | Asp | Leu | Leu | Lys | Leu | Ile | Glu | Asn | |
| | | 35 | | | | | 40 | | | | | 45 | | | | |

| aat | gcg | cgt | ctg | tgc | ggc | gtt | att | ttt | gac | tgg | gat | aaa | tat | aat | ctc | 192 |
|---|---|---|---|---|---|---|---|---|---|---|---|---|---|---|---|---|
| Asn | Ala | Arg | Leu | Cys | Gly | Val | Ile | Phe | Asp | Trp | Asp | Lys | Tyr | Asn | Leu | |
| 50 | | | | | 55 | | | | | 60 | | | | | | |

```
                                                    -continued
gag ctg tgc gaa gaa att agc aaa atg aac gag aac ctg ccg ttg tac      240
Glu Leu Cys Glu Glu Ile Ser Lys Met Asn Glu Asn Leu Pro Leu Tyr
 65                  70                  75                  80 gcg ttc gct aat acg tat tcc act ctc gat gta agc ctg aat gac ctg      288
Ala Phe Ala Asn Thr Tyr Ser Thr Leu Asp Val Ser Leu Asn Asp Leu
                     85                  90                  95 cgt tta cag att agc ttc ttt gaa tat gcg ctg ggt gct gct gaa gat      336
Arg Leu Gln Ile Ser Phe Phe Glu Tyr Ala Leu Gly Ala Ala Glu Asp
            100                 105                 110 att gct aat aag atc aag cag acc act gac gaa tat atc aac act att      384
Ile Ala Asn Lys Ile Lys Gln Thr Thr Asp Glu Tyr Ile Asn Thr Ile
        115                 120                 125 ctg cct ccg ctg act aaa gca ctg ttt aaa tat gtt cgt gaa ggt aaa      432
Leu Pro Pro Leu Thr Lys Ala Leu Phe Lys Tyr Val Arg Glu Gly Lys
    130                 135                 140 tat act ttc tgt act cct ggt cac atg ggc ggt act gca ttc cag aaa      480
Tyr Thr Phe Cys Thr Pro Gly His Met Gly Gly Thr Ala Phe Gln Lys
145                 150                 155                 160 agc ccg gta ggt agc ctg ttc tat gat ttc ttt ggt ccg aat acc atg      528
Ser Pro Val Gly Ser Leu Phe Tyr Asp Phe Phe Gly Pro Asn Thr Met
                165                 170                 175 aaa tct gat att tcc att tca gta tct gaa ctg ggt tct ctg ctg gat      576
Lys Ser Asp Ile Ser Ile Ser Val Ser Glu Leu Gly Ser Leu Leu Asp
            180                 185                 190 cac agt ggt cca cac aaa gaa gca gaa cag tat atc gct cgc gtc ttt      624
His Ser Gly Pro His Lys Glu Ala Glu Gln Tyr Ile Ala Arg Val Phe
        195                 200                 205 aac gca gac cgc agc tac atg gtg acc aac ggt act tcc act gcg aac      672
Asn Ala Asp Arg Ser Tyr Met Val Thr Asn Gly Thr Ser Thr Ala Asn
    210                 215                 220 aaa att gtt ggt atg tac tct gct cca gca ggc agc acc att ctg att      720
Lys Ile Val Gly Met Tyr Ser Ala Pro Ala Gly Ser Thr Ile Leu Ile
225                 230                 235                 240 gac cgt aac tgc cac aaa tcg ctg acc cac ctg atg atg atg agc gat      768
Asp Arg Asn Cys His Lys Ser Leu Thr His Leu Met Met Met Ser Asp
                245                 250                 255 gtt acg cca atc tat ttc cgc ccg acc cgt aac gct tac ggt att ctt      816
Val Thr Pro Ile Tyr Phe Arg Pro Thr Arg Asn Ala Tyr Gly Ile Leu
            260                 265                 270 ggt ggt atc cca cag agt gaa ttc cag cac gct acc att gct aag cgc      864
Gly Gly Ile Pro Gln Ser Glu Phe Gln His Ala Thr Ile Ala Lys Arg
        275                 280                 285 gtg aaa gaa aca cca aac gca acc tgg ccg gta cat gct gta att acc      912
Val Lys Glu Thr Pro Asn Ala Thr Trp Pro Val His Ala Val Ile Thr
    290                 295                 300 aac tct acc tat gat ggt ctg ctg tac aac acc gac ttc atc aag aaa      960
Asn Ser Thr Tyr Asp Gly Leu Leu Tyr Asn Thr Asp Phe Ile Lys Lys
305                 310                 315                 320 aca ctg gat gtg aaa tcc atc cac ttt gac tcc gcg tgg gtg cct tac     1008
Thr Leu Asp Val Lys Ser Ile His Phe Asp Ser Ala Trp Val Pro Tyr
                325                 330                 335 acc aac ttc tca ccg att tac gaa ggt aaa tgc ggt atg agc ggt ggc     1056
Thr Asn Phe Ser Pro Ile Tyr Glu Gly Lys Cys Gly Met Ser Gly Gly
            340                 345                 350 cgt gta gaa ggg aaa gtg att tac gaa acc cag tcc act cac aaa ctg     1104
Arg Val Glu Gly Lys Val Ile Tyr Glu Thr Gln Ser Thr His Lys Leu
        355                 360                 365 ctg gcg gcg ttc tct cag gct tcc atg atc cac gtt aaa ggt gac gta     1152
Leu Ala Ala Phe Ser Gln Ala Ser Met Ile His Val Lys Gly Asp Val
    370                 375                 380
```

```
                                -continued aac gaa gaa acc ttt aac gaa gcc tac atg atg cac acc acc act tct      1200
Asn Glu Glu Thr Phe Asn Glu Ala Tyr Met Met His Thr Thr Thr Ser
385                 390                 395                 400 ccg cac tac ggt atc gtg gcg tcc act gaa acc gct gcg gcg atg atg      1248
Pro His Tyr Gly Ile Val Ala Ser Thr Glu Thr Ala Ala Ala Met Met
                405                 410                 415 aaa ggc aat gca ggt aag cgt ctg atc aac ggt tct att gaa cgt gcg      1296
Lys Gly Asn Ala Gly Lys Arg Leu Ile Asn Gly Ser Ile Glu Arg Ala
            420                 425                 430 atc aaa ttc cgt aaa gag atc aaa cgt ctg aga acg gaa tct gat ggc      1344
Ile Lys Phe Arg Lys Glu Ile Lys Arg Leu Arg Thr Glu Ser Asp Gly
        435                 440                 445 tgg ttc ttt gat gta tgg cag ccg gat cat atc gat acg act gaa tgc      1392
Trp Phe Phe Asp Val Trp Gln Pro Asp His Ile Asp Thr Thr Glu Cys
    450                 455                 460 tgg ccg ctg cgt tct gac agc acc tgg cac ggc ttc aaa aac atc gat      1440
Trp Pro Leu Arg Ser Asp Ser Thr Trp His Gly Phe Lys Asn Ile Asp
465                 470                 475                 480 aac gag cac atg tat ctt gac ccg atc aaa gtc acc ctg ctg act ccg      1488
Asn Glu His Met Tyr Leu Asp Pro Ile Lys Val Thr Leu Leu Thr Pro
                485                 490                 495 ggg atg gaa aaa gac ggc acc atg agc gac ttt ggt att ccg gcc agc      1536
Gly Met Glu Lys Asp Gly Thr Met Ser Asp Phe Gly Ile Pro Ala Ser
            500                 505                 510 atc gtg gcg aaa tac ctc gac gaa cat ggc atc gtt gtt gag aaa acc      1584
Ile Val Ala Lys Tyr Leu Asp Glu His Gly Ile Val Val Glu Lys Thr
        515                 520                 525 ggt ccg tat aac ctg ctg ttc ctg ttc agc atc ggt atc gat aag acc      1632
Gly Pro Tyr Asn Leu Leu Phe Leu Phe Ser Ile Gly Ile Asp Lys Thr
    530                 535                 540 aaa gca ctg agc ctg ctg cgt gct ctg act gac ttt aaa cgt gcg ttc      1680
Lys Ala Leu Ser Leu Leu Arg Ala Leu Thr Asp Phe Lys Arg Ala Phe
545                 550                 555                 560 gac ctg aac ctg cgt gtg aaa aac atg ctg ccg tct ctg tat cgt gaa      1728
Asp Leu Asn Leu Arg Val Lys Asn Met Leu Pro Ser Leu Tyr Arg Glu
                565                 570                 575 gat cct gaa ttc tat gaa aac atg cgt att cag gaa ctg gct cag aat      1776
Asp Pro Glu Phe Tyr Glu Asn Met Arg Ile Gln Glu Leu Ala Gln Asn
            580                 585                 590 atc cac aaa ctg att gtt cac cac aat ctg ccg gat ctg atg tat cgc      1824
Ile His Lys Leu Ile Val His His Asn Leu Pro Asp Leu Met Tyr Arg
        595                 600                 605 gca ttt gaa gtg ctg ccg acg atg gta atg act ccg tat gct gca ttc      1872
Ala Phe Glu Val Leu Pro Thr Met Val Met Thr Pro Tyr Ala Ala Phe
    610                 615                 620 cag aaa gag ctg cac ggt atg acc gaa gaa gtt tac ctc gac gaa atg      1920
Gln Lys Glu Leu His Gly Met Thr Glu Glu Val Tyr Leu Asp Glu Met
625                 630                 635                 640 gta ggt cgt att aac gcc aat atg atc ctt ccg tac ccg ccg gga gtt      1968
Val Gly Arg Ile Asn Ala Asn Met Ile Leu Pro Tyr Pro Pro Gly Val
                645                 650                 655 cct ctg gta atg ccg ggt gaa atg atc acc gaa gaa agc cgt ccg gtt      2016
Pro Leu Val Met Pro Gly Glu Met Ile Thr Glu Glu Ser Arg Pro Val
            660                 665                 670 ctg gag ttc ctg cag atg ctg tgt gaa atc ggc gct cac tat ccg ggc      2064
Leu Glu Phe Leu Gln Met Leu Cys Glu Ile Gly Ala His Tyr Pro Gly
        675                 680                 685 ttt gaa acc gat att cac ggt gca tac cgt cag gct gat ggc cgc tat      2112
Phe Glu Thr Asp Ile His Gly Ala Tyr Arg Gln Ala Asp Gly Arg Tyr
    690                 695                 700
```

```
acc gtt aag gta ttg aaa gaa gaa agc aaa aaa taa                    2148
Thr Val Lys Val Leu Lys Glu Glu Ser Lys Lys
705             710             715

<210> SEQ ID NO 20
<211> LENGTH: 715
<212> TYPE: PRT
<213> ORGANISM: Escherichia coli

<400> SEQUENCE: 20

Met Asn Val Ile Ala Ile Leu Asn His Met Gly Val Tyr Phe Lys Glu
1               5                   10                  15

Glu Pro Ile Arg Glu Leu His Arg Ala Leu Glu Arg Leu Asn Phe Gln
            20                  25                  30

Ile Val Tyr Pro Asn Asp Arg Asp Leu Leu Lys Leu Ile Glu Asn
        35                  40                  45

Asn Ala Arg Leu Cys Gly Val Ile Phe Asp Trp Asp Lys Tyr Asn Leu
    50                  55                  60

Glu Leu Cys Glu Glu Ile Ser Lys Met Asn Glu Asn Leu Pro Leu Tyr
65                  70                  75                  80

Ala Phe Ala Asn Thr Tyr Ser Thr Leu Asp Val Ser Leu Asn Asp Leu
                85                  90                  95

Arg Leu Gln Ile Ser Phe Phe Glu Tyr Ala Leu Gly Ala Ala Glu Asp
            100                 105                 110

Ile Ala Asn Lys Ile Lys Gln Thr Thr Asp Glu Tyr Ile Asn Thr Ile
        115                 120                 125

Leu Pro Pro Leu Thr Lys Ala Leu Phe Lys Tyr Val Arg Glu Gly Lys
130                 135                 140

Tyr Thr Phe Cys Thr Pro Gly His Met Gly Gly Thr Ala Phe Gln Lys
145                 150                 155                 160

Ser Pro Val Gly Ser Leu Phe Tyr Asp Phe Phe Gly Pro Asn Thr Met
                165                 170                 175

Lys Ser Asp Ile Ser Ile Ser Val Ser Glu Leu Gly Ser Leu Leu Asp
            180                 185                 190

His Ser Gly Pro His Lys Glu Ala Glu Gln Tyr Ile Ala Arg Val Phe
        195                 200                 205

Asn Ala Asp Arg Ser Tyr Met Val Thr Asn Gly Thr Ser Thr Ala Asn
210                 215                 220

Lys Ile Val Gly Met Tyr Ser Ala Pro Ala Gly Ser Thr Ile Leu Ile
225                 230                 235                 240

Asp Arg Asn Cys His Lys Ser Leu Thr His Leu Met Met Met Ser Asp
                245                 250                 255

Val Thr Pro Ile Tyr Phe Arg Pro Thr Arg Asn Ala Tyr Gly Ile Leu
            260                 265                 270

Gly Gly Ile Pro Gln Ser Glu Phe Gln His Ala Thr Ile Ala Lys Arg
        275                 280                 285

Val Lys Glu Thr Pro Asn Ala Thr Trp Pro Val His Ala Val Ile Thr
290                 295                 300

Asn Ser Thr Tyr Asp Gly Leu Leu Tyr Asn Thr Asp Phe Ile Lys Lys
305                 310                 315                 320

Thr Leu Asp Val Lys Ser Ile His Phe Asp Ser Ala Trp Val Pro Tyr
                325                 330                 335

Thr Asn Phe Ser Pro Ile Tyr Glu Gly Lys Cys Gly Met Ser Gly Gly
            340                 345                 350

Arg Val Glu Gly Lys Val Ile Tyr Glu Thr Gln Ser Thr His Lys Leu
        355                 360                 365
```

```
Leu Ala Ala Phe Ser Gln Ala Ser Met Ile His Val Lys Gly Asp Val
        370                 375                 380

Asn Glu Glu Thr Phe Asn Glu Ala Tyr Met Met His Thr Thr Thr Ser
385                 390                 395                 400

Pro His Tyr Gly Ile Val Ala Ser Thr Glu Thr Ala Ala Ala Met Met
                405                 410                 415

Lys Gly Asn Ala Gly Lys Arg Leu Ile Asn Gly Ser Ile Glu Arg Ala
            420                 425                 430

Ile Lys Phe Arg Lys Glu Ile Lys Arg Leu Arg Thr Glu Ser Asp Gly
        435                 440                 445

Trp Phe Phe Asp Val Trp Gln Pro Asp His Ile Asp Thr Thr Glu Cys
    450                 455                 460

Trp Pro Leu Arg Ser Asp Ser Thr Trp His Gly Phe Lys Asn Ile Asp
465                 470                 475                 480

Asn Glu His Met Tyr Leu Asp Pro Ile Lys Val Thr Leu Leu Thr Pro
                485                 490                 495

Gly Met Glu Lys Asp Gly Thr Met Ser Asp Phe Gly Ile Pro Ala Ser
            500                 505                 510

Ile Val Ala Lys Tyr Leu Asp Glu His Gly Ile Val Val Glu Lys Thr
        515                 520                 525

Gly Pro Tyr Asn Leu Leu Phe Leu Phe Ser Ile Gly Ile Asp Lys Thr
    530                 535                 540

Lys Ala Leu Ser Leu Leu Arg Ala Leu Thr Asp Phe Lys Arg Ala Phe
545                 550                 555                 560

Asp Leu Asn Leu Arg Val Lys Asn Met Leu Pro Ser Leu Tyr Arg Glu
                565                 570                 575

Asp Pro Glu Phe Tyr Glu Asn Met Arg Ile Gln Glu Leu Ala Gln Asn
            580                 585                 590

Ile His Lys Leu Ile Val His His Asn Leu Pro Asp Leu Met Tyr Arg
        595                 600                 605

Ala Phe Glu Val Leu Pro Thr Met Val Met Thr Pro Tyr Ala Ala Phe
    610                 615                 620

Gln Lys Glu Leu His Gly Met Thr Glu Glu Val Tyr Leu Asp Glu Met
625                 630                 635                 640

Val Gly Arg Ile Asn Ala Asn Met Ile Leu Pro Tyr Pro Pro Gly Val
                645                 650                 655

Pro Leu Val Met Pro Gly Glu Met Ile Thr Glu Glu Ser Arg Pro Val
            660                 665                 670

Leu Glu Phe Leu Gln Met Leu Cys Glu Ile Gly Ala His Tyr Pro Gly
        675                 680                 685

Phe Glu Thr Asp Ile His Gly Ala Tyr Arg Gln Ala Asp Gly Arg Tyr
    690                 695                 700

Thr Val Lys Val Leu Lys Glu Glu Ser Lys Lys
705                 710                 715

<210> SEQ ID NO 21
<211> LENGTH: 2142
<212> TYPE: DNA
<213> ORGANISM: Escherichia coli
<220> FEATURE:
<221> NAME/KEY: CDS
<222> LOCATION: (1)..(2139)

<400> SEQUENCE: 21 atg aac atc att gcc att atg gga ccg cat ggc gtc ttt tat aaa gat      48
Met Asn Ile Ile Ala Ile Met Gly Pro His Gly Val Phe Tyr Lys Asp
1               5                   10                  15
```

```
                                          -continued gag ccc atc aaa gaa ctg gag tcg gcg ctg gtg gcg caa ggc ttt cag      96
Glu Pro Ile Lys Glu Leu Glu Ser Ala Leu Val Ala Gln Gly Phe Gln
         20              25              30 att atc tgg cca caa aac agc gtt gat ttg ctg aaa ttt atc gag cat     144
Ile Ile Trp Pro Gln Asn Ser Val Asp Leu Leu Lys Phe Ile Glu His
     35              40              45 aac cct cga att tgc ggc gtg att ttt gac tgg gat gag tac agt ctc     192
Asn Pro Arg Ile Cys Gly Val Ile Phe Asp Trp Asp Glu Tyr Ser Leu
 50              55              60 gat tta tgt agc gat atc aat cag ctt aat gaa tat ctc ccg ctt tat     240
Asp Leu Cys Ser Asp Ile Asn Gln Leu Asn Glu Tyr Leu Pro Leu Tyr
 65              70              75              80 gcc ttc atc aac acc cac tcg acg atg gat gtc agc gtg cag gat atg     288
Ala Phe Ile Asn Thr His Ser Thr Met Asp Val Ser Val Gln Asp Met
             85              90              95 cgg atg gcg ctc tgg ttt ttt gaa tat gcg ctg ggg cag gcg gaa gat     336
Arg Met Ala Leu Trp Phe Phe Glu Tyr Ala Leu Gly Gln Ala Glu Asp
             100             105             110 atc gcc att cgt atg cgt cag tac acc gac gaa tat ctt gat aac att     384
Ile Ala Ile Arg Met Arg Gln Tyr Thr Asp Glu Tyr Leu Asp Asn Ile
             115             120             125 aca ccg ccg ttc acg aaa gcc ttg ttt acc tac gtc aaa gag cgg aag     432
Thr Pro Pro Phe Thr Lys Ala Leu Phe Thr Tyr Val Lys Glu Arg Lys
 130             135             140 tac acc ttt tgt acg ccg ggg cat atg ggc ggc acc gca tat caa aaa     480
Tyr Thr Phe Cys Thr Pro Gly His Met Gly Gly Thr Ala Tyr Gln Lys
145             150             155             160 agc ccg gtt ggc tgt ctg ttt tat gat ttt ttc ggc ggg aat act ctt     528
Ser Pro Val Gly Cys Leu Phe Tyr Asp Phe Phe Gly Gly Asn Thr Leu
             165             170             175 aag gct gat gtc tct att tcg gtc acc gag ctt ggt tcg ttg ctc gac     576
Lys Ala Asp Val Ser Ile Ser Val Thr Glu Leu Gly Ser Leu Leu Asp
             180             185             190 cac acc ggg cca cac ctg gaa gcg gaa gag tac atc gcg cgg act ttt     624
His Thr Gly Pro His Leu Glu Ala Glu Glu Tyr Ile Ala Arg Thr Phe
             195             200             205 ggc gcg gaa cag agt tat atc gtt acc aac gga aca tcg acg tcg aac     672
Gly Ala Glu Gln Ser Tyr Ile Val Thr Asn Gly Thr Ser Thr Ser Asn
 210             215             220 aaa att gtg ggt atg tac gcc gcg cca tcc ggc agt acg ctg ttg atc     720
Lys Ile Val Gly Met Tyr Ala Ala Pro Ser Gly Ser Thr Leu Leu Ile
225             230             235             240 gac cgc aat tgt cat aaa tcg ctg gcg cat ctg ttg atg atg aac gat     768
Asp Arg Asn Cys His Lys Ser Leu Ala His Leu Leu Met Met Asn Asp
             245             250             255 gta gtg cca gtc tgg ctg aaa ccg acg cgt aat gcg ttg ggg att ctt     816
Val Val Pro Val Trp Leu Lys Pro Thr Arg Asn Ala Leu Gly Ile Leu
             260             265             270 ggt ggg atc ccg cgc cgt gaa ttt act cgc gac agc atc gaa gag aaa     864
Gly Gly Ile Pro Arg Arg Glu Phe Thr Arg Asp Ser Ile Glu Glu Lys
             275             280             285 gtc gct gct acc acg caa gca caa tgg ccg gtt cat gcg gtg atc acc     912
Val Ala Ala Thr Thr Gln Ala Gln Trp Pro Val His Ala Val Ile Thr
 290             295             300 aac tcc acc tat gat ggc ttg ctc tac aac acc gac tgg atc aaa cag     960
Asn Ser Thr Tyr Asp Gly Leu Leu Tyr Asn Thr Asp Trp Ile Lys Gln
305             310             315             320 acg ctg gat gtc ccg tcg att cac ttc gat tct gcc tgg gtg ccg tac    1008
Thr Leu Asp Val Pro Ser Ile His Phe Asp Ser Ala Trp Val Pro Tyr
             325             330             335
```

```
acc cat ttt cat ccg atc tac cag ggt aaa agt ggt atg agc ggc gag        1056
Thr His Phe His Pro Ile Tyr Gln Gly Lys Ser Gly Met Ser Gly Glu
        340                 345                 350 cgt gtt gcg gga aaa gtg atc ttc gaa acg caa tcg acc cac aaa atg        1104
Arg Val Ala Gly Lys Val Ile Phe Glu Thr Gln Ser Thr His Lys Met
    355                 360                 365 ctg gcg gcg tta tcg cag gct tcg ctg atc cac att aaa ggc gag tat        1152
Leu Ala Ala Leu Ser Gln Ala Ser Leu Ile His Ile Lys Gly Glu Tyr
370                 375                 380 gac gaa gag gcc ttt aac gaa gcc ttt atg atg cat acc acc acc tcg        1200
Asp Glu Glu Ala Phe Asn Glu Ala Phe Met Met His Thr Thr Thr Ser
385                 390                 395                 400 ccc agt tat ccc att gtt gct tcg gtt gag acg gcg gcg gcg atg ctg        1248
Pro Ser Tyr Pro Ile Val Ala Ser Val Glu Thr Ala Ala Ala Met Leu
                405                 410                 415 cgt ggt aat ccg ggc aaa cgg ctg att aac cgt tca gta gaa cga gct        1296
Arg Gly Asn Pro Gly Lys Arg Leu Ile Asn Arg Ser Val Glu Arg Ala
            420                 425                 430 ctg cat ttt cgc aaa gag gtc cag cgg ctg cgg gaa gag tct gac ggt        1344
Leu His Phe Arg Lys Glu Val Gln Arg Leu Arg Glu Glu Ser Asp Gly
        435                 440                 445 tgg ttt ttc gat atc tgg caa ccg ccg cag gtg gat gaa gcc gaa tgc        1392
Trp Phe Phe Asp Ile Trp Gln Pro Pro Gln Val Asp Glu Ala Glu Cys
450                 455                 460 tgg ccc gtt gcg cct ggc gaa cag tgg cac ggc ttt aac gat gcg gat        1440
Trp Pro Val Ala Pro Gly Glu Gln Trp His Gly Phe Asn Asp Ala Asp
465                 470                 475                 480 gcc gat cat atg ttt ctc gat ccg gtt aaa gtc act att ttg aca ccg        1488
Ala Asp His Met Phe Leu Asp Pro Val Lys Val Thr Ile Leu Thr Pro
                485                 490                 495 ggg atg gac gag cag ggc aat atg agc gag gag ggg atc ccg gcg gcg        1536
Gly Met Asp Glu Gln Gly Asn Met Ser Glu Glu Gly Ile Pro Ala Ala
            500                 505                 510 ctg gta gca aaa ttc ctc gac gaa cgt ggg atc gta gta gag aaa acc        1584
Leu Val Ala Lys Phe Leu Asp Glu Arg Gly Ile Val Val Glu Lys Thr
        515                 520                 525 ggc cct tat aac ctg ctg ttt ctc ttt agt att ggc atc gat aaa acc        1632
Gly Pro Tyr Asn Leu Leu Phe Leu Phe Ser Ile Gly Ile Asp Lys Thr
530                 535                 540 aaa gca atg gga tta ttg cgt ggg ttg acg gaa ttc aaa cgc tct tac        1680
Lys Ala Met Gly Leu Leu Arg Gly Leu Thr Glu Phe Lys Arg Ser Tyr
545                 550                 555                 560 gat ctc aac ctg cgg atc aaa aat atg cta ccc gat ctc tat gca gaa        1728
Asp Leu Asn Leu Arg Ile Lys Asn Met Leu Pro Asp Leu Tyr Ala Glu
                565                 570                 575 gat ccc gat ttc tac cgc aat atg cgt att cag gat ctg gca caa ggg        1776
Asp Pro Asp Phe Tyr Arg Asn Met Arg Ile Gln Asp Leu Ala Gln Gly
            580                 585                 590 atc cat aag ctg att cgt aaa cac gat ctt ccc ggt ttg atg ttg cgg        1824
Ile His Lys Leu Ile Arg Lys His Asp Leu Pro Gly Leu Met Leu Arg
        595                 600                 605 gca ttc gat act ttg ccg gag atg atc atg acg cca cat cag gca tgg        1872
Ala Phe Asp Thr Leu Pro Glu Met Ile Met Thr Pro His Gln Ala Trp
610                 615                 620 caa cga caa att aaa ggc gaa gta gaa acc att gcg ctg gaa caa ctg        1920
Gln Arg Gln Ile Lys Gly Glu Val Glu Thr Ile Ala Leu Glu Gln Leu
625                 630                 635                 640 gtc ggt aga gta tcg gca aat atg atc ctg cct tat cca ccg ggc gta        1968
Val Gly Arg Val Ser Ala Asn Met Ile Leu Pro Tyr Pro Pro Gly Val
                645                 650                 655
```

```
ccg ctg ttg atg cct gga gaa atg ctg acc aaa gag agc cgc aca gta     2016
Pro Leu Leu Met Pro Gly Glu Met Leu Thr Lys Glu Ser Arg Thr Val
        660                 665                 670 ctc gat ttt cta ctg atg ctt tgt tcc gtc ggg caa cat tac ccc ggt     2064
Leu Asp Phe Leu Leu Met Leu Cys Ser Val Gly Gln His Tyr Pro Gly
        675                 680                 685 ttt gaa acg gat att cac ggc gcg aaa cag gac gaa gac ggc gtt tac     2112
Phe Glu Thr Asp Ile His Gly Ala Lys Gln Asp Glu Asp Gly Val Tyr
        690                 695                 700 cgc gta cga gtc cta aaa atg gcg gga taa                             2142
Arg Val Arg Val Leu Lys Met Ala Gly
705             710
```

<210> SEQ ID NO 22
<211> LENGTH: 713
<212> TYPE: PRT
<213> ORGANISM: Escherichia coli

<400> SEQUENCE: 22

```
Met Asn Ile Ile Ala Ile Met Gly Pro His Gly Val Phe Tyr Lys Asp
1               5                   10                  15

Glu Pro Ile Lys Glu Leu Glu Ser Ala Leu Val Ala Gln Gly Phe Gln
            20                  25                  30

Ile Ile Trp Pro Gln Asn Ser Val Asp Leu Leu Lys Phe Ile Glu His
        35                  40                  45

Asn Pro Arg Ile Cys Gly Val Ile Phe Asp Trp Asp Glu Tyr Ser Leu
    50                  55                  60

Asp Leu Cys Ser Asp Ile Asn Gln Leu Asn Glu Tyr Leu Pro Leu Tyr
65                  70                  75                  80

Ala Phe Ile Asn Thr His Ser Thr Met Asp Val Ser Val Gln Asp Met
                85                  90                  95

Arg Met Ala Leu Trp Phe Phe Glu Tyr Ala Leu Gly Gln Ala Glu Asp
            100                 105                 110

Ile Ala Ile Arg Met Arg Gln Tyr Thr Asp Glu Tyr Leu Asp Asn Ile
        115                 120                 125

Thr Pro Pro Phe Thr Lys Ala Leu Phe Thr Tyr Val Lys Glu Arg Lys
    130                 135                 140

Tyr Thr Phe Cys Thr Pro Gly His Met Gly Gly Thr Ala Tyr Gln Lys
145                 150                 155                 160

Ser Pro Val Gly Cys Leu Phe Tyr Asp Phe Phe Gly Gly Asn Thr Leu
                165                 170                 175

Lys Ala Asp Val Ser Ile Ser Val Thr Glu Leu Gly Ser Leu Leu Asp
            180                 185                 190

His Thr Gly Pro His Leu Glu Ala Glu Glu Tyr Ile Ala Arg Thr Phe
        195                 200                 205

Gly Ala Glu Gln Ser Tyr Ile Val Thr Asn Gly Thr Ser Thr Ser Asn
    210                 215                 220

Lys Ile Val Gly Met Tyr Ala Ala Pro Ser Gly Ser Thr Leu Leu Ile
225                 230                 235                 240

Asp Arg Asn Cys His Lys Ser Leu Ala His Leu Leu Met Met Asn Asp
                245                 250                 255

Val Val Pro Val Trp Leu Lys Pro Thr Arg Asn Ala Leu Gly Ile Leu
            260                 265                 270

Gly Gly Ile Pro Arg Arg Glu Phe Thr Arg Asp Ser Ile Glu Glu Lys
        275                 280                 285

Val Ala Ala Thr Thr Gln Ala Gln Trp Pro Val His Ala Val Ile Thr
    290                 295                 300
```

-continued

Asn Ser Thr Tyr Asp Gly Leu Leu Tyr Asn Thr Asp Trp Ile Lys Gln
305                 310                 315                 320

Thr Leu Asp Val Pro Ser Ile His Phe Asp Ser Ala Trp Val Pro Tyr
                325                 330                 335

Thr His Phe His Pro Ile Tyr Gln Gly Lys Ser Gly Met Ser Gly Glu
            340                 345                 350

Arg Val Ala Gly Lys Val Ile Phe Glu Thr Gln Ser Thr His Lys Met
        355                 360                 365

Leu Ala Ala Leu Ser Gln Ala Ser Leu Ile His Ile Lys Gly Glu Tyr
370                 375                 380

Asp Glu Glu Ala Phe Asn Glu Ala Phe Met Met His Thr Thr Thr Ser
385                 390                 395                 400

Pro Ser Tyr Pro Ile Val Ala Ser Val Glu Thr Ala Ala Ala Met Leu
                405                 410                 415

Arg Gly Asn Pro Gly Lys Arg Leu Ile Asn Arg Ser Val Glu Arg Ala
            420                 425                 430

Leu His Phe Arg Lys Glu Val Gln Arg Leu Arg Glu Glu Ser Asp Gly
        435                 440                 445

Trp Phe Phe Asp Ile Trp Gln Pro Pro Gln Val Asp Glu Ala Glu Cys
450                 455                 460

Trp Pro Val Ala Pro Gly Glu Gln Trp His Gly Phe Asn Asp Ala Asp
465                 470                 475                 480

Ala Asp His Met Phe Leu Asp Pro Val Lys Val Thr Ile Leu Thr Pro
                485                 490                 495

Gly Met Asp Glu Gln Gly Asn Met Ser Glu Glu Gly Ile Pro Ala Ala
            500                 505                 510

Leu Val Ala Lys Phe Leu Asp Glu Arg Gly Ile Val Val Glu Lys Thr
        515                 520                 525

Gly Pro Tyr Asn Leu Leu Phe Leu Phe Ser Ile Gly Ile Asp Lys Thr
530                 535                 540

Lys Ala Met Gly Leu Leu Arg Gly Leu Thr Glu Phe Lys Arg Ser Tyr
545                 550                 555                 560

Asp Leu Asn Leu Arg Ile Lys Asn Met Leu Pro Asp Leu Tyr Ala Glu
                565                 570                 575

Asp Pro Asp Phe Tyr Arg Asn Met Arg Ile Gln Asp Leu Ala Gln Gly
            580                 585                 590

Ile His Lys Leu Ile Arg Lys His Asp Leu Pro Gly Leu Met Leu Arg
        595                 600                 605

Ala Phe Asp Thr Leu Pro Glu Met Ile Met Thr Pro His Gln Ala Trp
610                 615                 620

Gln Arg Gln Ile Lys Gly Glu Val Glu Thr Ile Ala Leu Glu Gln Leu
625                 630                 635                 640

Val Gly Arg Val Ser Ala Asn Met Ile Leu Pro Tyr Pro Pro Gly Val
                645                 650                 655

Pro Leu Leu Met Pro Gly Glu Met Leu Thr Lys Glu Ser Arg Thr Val
            660                 665                 670

Leu Asp Phe Leu Leu Met Leu Cys Ser Val Gly Gln His Tyr Pro Gly
        675                 680                 685

Phe Glu Thr Asp Ile His Gly Ala Lys Gln Asp Glu Asp Gly Val Tyr
690                 695                 700

Arg Val Arg Val Leu Lys Met Ala Gly
705                 710

<210> SEQ ID NO 23
<211> LENGTH: 1101
<212> TYPE: DNA
<213> ORGANISM: Escherichia coli
<220> FEATURE:
<221> NAME/KEY: CDS
<222> LOCATION: (1)..(1098)

<400> SEQUENCE: 23

| | | | | | | | | | | | | | | | | |
|---|---|---|---|---|---|---|---|---|---|---|---|---|---|---|---|---|
| atg | tca | aat | gct | caa | gag | gcg | gta | aaa | acc | cgc | cac | aag | gag | act | tcg | 48 |
| Met | Ser | Asn | Ala | Gln | Glu | Ala | Val | Lys | Thr | Arg | His | Lys | Glu | Thr | Ser | |
| 1 | | | | 5 | | | | | 10 | | | | | 15 | | |
| ctt | att | ttc | ccg | gtt | ctg | gcg | ctg | gta | gtg | ctg | ttc | ctg | tgg | gga | agc | 96 |
| Leu | Ile | Phe | Pro | Val | Leu | Ala | Leu | Val | Val | Leu | Phe | Leu | Trp | Gly | Ser | |
| | | | 20 | | | | | 25 | | | | | 30 | | | |
| agc | cag | aca | cta | cca | gtg | gtc | att | gcc | atc | aat | ctt | ctt | gcg | ctt | att | 144 |
| Ser | Gln | Thr | Leu | Pro | Val | Val | Ile | Ala | Ile | Asn | Leu | Leu | Ala | Leu | Ile | |
| | | 35 | | | | | 40 | | | | | 45 | | | | |
| ggt | att | tta | agt | agc | gcc | ttt | agt | gtt | gtc | cgt | cat | gcg | gac | gta | tta | 192 |
| Gly | Ile | Leu | Ser | Ser | Ala | Phe | Ser | Val | Val | Arg | His | Ala | Asp | Val | Leu | |
| | 50 | | | | | 55 | | | | | 60 | | | | | |
| gcc | cat | cgc | ctg | gga | gaa | cct | tac | ggt | tcg | ctt | att | ctt | agc | ctt | tca | 240 |
| Ala | His | Arg | Leu | Gly | Glu | Pro | Tyr | Gly | Ser | Leu | Ile | Leu | Ser | Leu | Ser | |
| 65 | | | | | 70 | | | | | 75 | | | | | 80 | |
| gtg | gtt | att | ctt | gaa | gtc | agt | ttg | att | tca | gct | tta | atg | gca | acc | ggc | 288 |
| Val | Val | Ile | Leu | Glu | Val | Ser | Leu | Ile | Ser | Ala | Leu | Met | Ala | Thr | Gly | |
| | | | | 85 | | | | | 90 | | | | | 95 | | |
| gac | gcc | gcg | cca | acg | cta | atg | cgt | gat | acg | ctc | tat | tca | atc | att | atg | 336 |
| Asp | Ala | Ala | Pro | Thr | Leu | Met | Arg | Asp | Thr | Leu | Tyr | Ser | Ile | Ile | Met | |
| | | | 100 | | | | | 105 | | | | | 110 | | | |
| att | gtt | acc | ggt | ggg | ctg | gtt | ggc | ttt | tca | tta | ttg | ttg | ggc | ggt | cgt | 384 |
| Ile | Val | Thr | Gly | Gly | Leu | Val | Gly | Phe | Ser | Leu | Leu | Leu | Gly | Gly | Arg | |
| | | 115 | | | | | 120 | | | | | 125 | | | | |
| aag | ttt | gcc | acc | caa | tat | atg | aat | ctg | ttt | ggt | atc | aag | cag | tat | tta | 432 |
| Lys | Phe | Ala | Thr | Gln | Tyr | Met | Asn | Leu | Phe | Gly | Ile | Lys | Gln | Tyr | Leu | |
| | 130 | | | | | 135 | | | | | 140 | | | | | |
| att | gcg | ctg | ttc | ccc | ctg | gcg | ata | atc | gta | ctg | gta | ttt | cca | atg | gct | 480 |
| Ile | Ala | Leu | Phe | Pro | Leu | Ala | Ile | Ile | Val | Leu | Val | Phe | Pro | Met | Ala | |
| 145 | | | | | 150 | | | | | 155 | | | | | 160 | |
| ctg | cct | gcg | gcg | aat | ttt | tca | acc | ggt | cag | gcg | tta | ctg | gta | gca | tta | 528 |
| Leu | Pro | Ala | Ala | Asn | Phe | Ser | Thr | Gly | Gln | Ala | Leu | Leu | Val | Ala | Leu | |
| | | | | 165 | | | | | 170 | | | | | 175 | | |
| att | tct | gcg | gca | atg | tat | ggc | gta | ttt | ttg | ctg | atc | cag | acc | aaa | acg | 576 |
| Ile | Ser | Ala | Ala | Met | Tyr | Gly | Val | Phe | Leu | Leu | Ile | Gln | Thr | Lys | Thr | |
| | | | | 180 | | | | | 185 | | | | | 190 | | |
| cat | caa | agt | ttg | ttt | gtc | tac | gag | cac | gaa | gat | gac | agt | gat | gat | gac | 624 |
| His | Gln | Ser | Leu | Phe | Val | Tyr | Glu | His | Glu | Asp | Asp | Ser | Asp | Asp | Asp | |
| | | 195 | | | | | 200 | | | | | 205 | | | | |
| gac | ccg | cat | cac | ggt | aaa | ccg | tct | gcc | cat | agc | agc | ctg | tgg | cat | gct | 672 |
| Asp | Pro | His | His | Gly | Lys | Pro | Ser | Ala | His | Ser | Ser | Leu | Trp | His | Ala | |
| | 210 | | | | | 215 | | | | | 220 | | | | | |
| atc | tgg | ttg | att | atc | cat | ctg | att | gcc | gtt | att | gcg | gtg | acc | aaa | atg | 720 |
| Ile | Trp | Leu | Ile | Ile | His | Leu | Ile | Ala | Val | Ile | Ala | Val | Thr | Lys | Met | |
| 225 | | | | | 230 | | | | | 235 | | | | | 240 | |
| aac | gcc | agc | tcg | ctg | gag | aca | ttg | ctc | gac | agc | atg | aat | gcc | cct | gtc | 768 |
| Asn | Ala | Ser | Ser | Leu | Glu | Thr | Leu | Leu | Asp | Ser | Met | Asn | Ala | Pro | Val | |
| | | | | 245 | | | | | 250 | | | | | 255 | | |
| gcc | ttt | act | ggc | ttc | ctg | gtg | gca | ctg | ttg | att | ctg | tcg | ccg | gaa | ggt | 816 |
| Ala | Phe | Thr | Gly | Phe | Leu | Val | Ala | Leu | Leu | Ile | Leu | Ser | Pro | Glu | Gly | |
| | | | | 260 | | | | | 265 | | | | | 270 | | |

```
tta ggt gca tta aaa gca gtg ttg aac aac cag gtt cag cgc gcg atg        864
Leu Gly Ala Leu Lys Ala Val Leu Asn Asn Gln Val Gln Arg Ala Met
            275                 280                 285 aat ctg ttc ttt ggt tca gtg tta gca acc att tcg ctt acc gta cct        912
Asn Leu Phe Phe Gly Ser Val Leu Ala Thr Ile Ser Leu Thr Val Pro
        290                 295                 300 gtc gtc acg cta att gcc ttt atg acg ggt aac gaa ttg cag ttt gca        960
Val Val Thr Leu Ile Ala Phe Met Thr Gly Asn Glu Leu Gln Phe Ala
305                 310                 315                 320 ctt ggt gcg cca gaa atg gtg gtg atg gtg gcc tct tta gtg ctg tgc       1008
Leu Gly Ala Pro Glu Met Val Val Met Val Ala Ser Leu Val Leu Cys
                325                 330                 335 cat atc tcc ttc tcc acc gga cgt act aac gtg ctc aat ggc gca gcg       1056
His Ile Ser Phe Ser Thr Gly Arg Thr Asn Val Leu Asn Gly Ala Ala
            340                 345                 350 cat ctg gca ctg ttt gcc gcc tat ttg atg acg ata ttt gcc tga           1101
His Leu Ala Leu Phe Ala Ala Tyr Leu Met Thr Ile Phe Ala
        355                 360                 365
```

<210> SEQ ID NO 24
<211> LENGTH: 366
<212> TYPE: PRT
<213> ORGANISM: Escherichia coli

<400> SEQUENCE: 24

```
Met Ser Asn Ala Gln Glu Ala Val Lys Thr Arg His Lys Glu Thr Ser
1               5                   10                  15

Leu Ile Phe Pro Val Leu Ala Leu Val Val Leu Phe Leu Trp Gly Ser
                20                  25                  30

Ser Gln Thr Leu Pro Val Val Ile Ala Ile Asn Leu Leu Ala Leu Ile
            35                  40                  45

Gly Ile Leu Ser Ser Ala Phe Ser Val Val Arg His Ala Asp Val Leu
        50                  55                  60

Ala His Arg Leu Gly Glu Pro Tyr Gly Ser Leu Ile Leu Ser Leu Ser
65                  70                  75                  80

Val Val Ile Leu Glu Val Ser Leu Ile Ser Ala Leu Met Ala Thr Gly
                85                  90                  95

Asp Ala Ala Pro Thr Leu Met Arg Asp Thr Leu Tyr Ser Ile Ile Met
                100                 105                 110

Ile Val Thr Gly Gly Leu Val Gly Phe Ser Leu Leu Leu Gly Gly Arg
        115                 120                 125

Lys Phe Ala Thr Gln Tyr Met Asn Leu Phe Gly Ile Lys Gln Tyr Leu
    130                 135                 140

Ile Ala Leu Phe Pro Leu Ala Ile Ile Val Leu Val Phe Pro Met Ala
145                 150                 155                 160

Leu Pro Ala Ala Asn Phe Ser Thr Gly Gln Ala Leu Leu Val Ala Leu
                165                 170                 175

Ile Ser Ala Ala Met Tyr Gly Val Phe Leu Leu Ile Gln Thr Lys Thr
            180                 185                 190

His Gln Ser Leu Phe Val Tyr Glu His Glu Asp Ser Asp Asp Asp
        195                 200                 205

Asp Pro His His Gly Lys Pro Ser Ala His Ser Ser Leu Trp His Ala
    210                 215                 220

Ile Trp Leu Ile Ile His Leu Ile Ala Val Ile Ala Val Thr Lys Met
225                 230                 235                 240

Asn Ala Ser Ser Leu Glu Thr Leu Leu Asp Ser Met Asn Ala Pro Val
                245                 250                 255
```

```
Ala Phe Thr Gly Phe Leu Val Ala Leu Leu Ile Leu Ser Pro Glu Gly
            260                 265                 270

Leu Gly Ala Leu Lys Ala Val Leu Asn Asn Gln Val Gln Arg Ala Met
        275                 280                 285

Asn Leu Phe Phe Gly Ser Val Leu Ala Thr Ile Ser Leu Thr Val Pro
        290                 295                 300

Val Val Thr Leu Ile Ala Phe Met Thr Gly Asn Glu Leu Gln Phe Ala
305                 310                 315                 320

Leu Gly Ala Pro Glu Met Val Met Val Ala Ser Leu Val Leu Cys
            325                 330                 335

His Ile Ser Phe Ser Thr Gly Arg Thr Asn Val Leu Asn Gly Ala Ala
            340                 345                 350

His Leu Ala Leu Phe Ala Ala Tyr Leu Met Thr Ile Phe Ala
            355                 360                 365

<210> SEQ ID NO 25
<211> LENGTH: 1233
<212> TYPE: DNA
<213> ORGANISM: Escherichia coli
<220> FEATURE:
<221> NAME/KEY: CDS
<222> LOCATION: (1)..(1230)

<400> SEQUENCE: 25
```

| | | | | | | | | | | | | | | | | |
|---|---|---|---|---|---|---|---|---|---|---|---|---|---|---|---|---|
| atg | caa | aat | aaa | tta | gct | tcc | ggt | gcc | agg | ctt | gga | cgt | cag | gcg | tta | 48 |
| Met | Gln | Asn | Lys | Leu | Ala | Ser | Gly | Ala | Arg | Leu | Gly | Arg | Gln | Ala | Leu | |
| 1 | | | | 5 | | | | | 10 | | | | | 15 | | |
| ctt | ttc | cct | ctc | tgt | ctg | gtg | ctt | tac | gaa | ttt | tca | acc | tat | atc | ggc | 96 |
| Leu | Phe | Pro | Leu | Cys | Leu | Val | Leu | Tyr | Glu | Phe | Ser | Thr | Tyr | Ile | Gly | |
| | | | 20 | | | | | 25 | | | | | 30 | | | |
| aac | gat | atg | att | caa | ccc | ggt | atg | ttg | gcc | gtg | gtg | gaa | caa | tat | cag | 144 |
| Asn | Asp | Met | Ile | Gln | Pro | Gly | Met | Leu | Ala | Val | Val | Glu | Gln | Tyr | Gln | |
| | | | 35 | | | | 40 | | | | | 45 | | | | |
| gcg | ggc | att | gat | tgg | gtt | cct | act | tcg | atg | acc | gcg | tat | ctg | gcg | ggc | 192 |
| Ala | Gly | Ile | Asp | Trp | Val | Pro | Thr | Ser | Met | Thr | Ala | Tyr | Leu | Ala | Gly | |
| | 50 | | | | | 55 | | | | | 60 | | | | | |
| ggg | atg | ttt | tta | caa | tgg | ctg | ctg | ggg | ccg | ctg | tcg | gat | cgt | att | ggt | 240 |
| Gly | Met | Phe | Leu | Gln | Trp | Leu | Leu | Gly | Pro | Leu | Ser | Asp | Arg | Ile | Gly | |
| 65 | | | | | 70 | | | | | 75 | | | | | 80 | |
| cgc | cgt | ccg | gtg | atg | ctg | gcg | gga | gtg | gtg | tgg | ttt | atc | gtc | acc | tgt | 288 |
| Arg | Arg | Pro | Val | Met | Leu | Ala | Gly | Val | Val | Trp | Phe | Ile | Val | Thr | Cys | |
| | | | | 85 | | | | | 90 | | | | | 95 | | |
| ctg | gca | ata | ttg | ctg | gcg | caa | aac | att | gaa | caa | ttc | acc | ctg | ttg | cgc | 336 |
| Leu | Ala | Ile | Leu | Leu | Ala | Gln | Asn | Ile | Glu | Gln | Phe | Thr | Leu | Leu | Arg | |
| | | | 100 | | | | | 105 | | | | | 110 | | | |
| ttc | ttg | cag | ggc | ata | agc | ctc | tgt | ttc | att | ggc | gct | gtg | gga | tac | gcc | 384 |
| Phe | Leu | Gln | Gly | Ile | Ser | Leu | Cys | Phe | Ile | Gly | Ala | Val | Gly | Tyr | Ala | |
| | | | 115 | | | | | 120 | | | | | 125 | | | |
| gca | att | cag | gaa | tcc | ttc | gaa | gag | gcg | gtt | tgt | atc | aag | atc | acc | gcg | 432 |
| Ala | Ile | Gln | Glu | Ser | Phe | Glu | Glu | Ala | Val | Cys | Ile | Lys | Ile | Thr | Ala | |
| | | 130 | | | | | 135 | | | | | 140 | | | | |
| ctg | atg | gcg | aac | gtg | gcg | ctg | att | gct | ccg | cta | ctt | ggt | ccg | ctg | gtg | 480 |
| Leu | Met | Ala | Asn | Val | Ala | Leu | Ile | Ala | Pro | Leu | Leu | Gly | Pro | Leu | Val | |
| 145 | | | | | 150 | | | | | 155 | | | | | 160 | |
| ggc | gcg | gcg | tgg | atc | cat | gtg | ctg | ccc | tgg | gag | ggg | atg | ttt | gtt | ttg | 528 |
| Gly | Ala | Ala | Trp | Ile | His | Val | Leu | Pro | Trp | Glu | Gly | Met | Phe | Val | Leu | |
| | | | | 165 | | | | | 170 | | | | | 175 | | |
| ttt | gcc | gca | ttg | gca | gcg | atc | tcc | ttt | ttc | ggt | ctg | caa | cga | gcc | atg | 576 |
| Phe | Ala | Ala | Leu | Ala | Ala | Ile | Ser | Phe | Phe | Gly | Leu | Gln | Arg | Ala | Met | |
| | | | 180 | | | | | 185 | | | | | 190 | | | |

```
cct gaa acc gcc acg cgt ata ggc gag aaa ctg tca ctg aaa gaa ctc      624
Pro Glu Thr Ala Thr Arg Ile Gly Glu Lys Leu Ser Leu Lys Glu Leu
            195                 200                 205 ggt cgt gac tat aag ctg gtg ctg aag aac ggc cgc ttt gtg gcg ggg      672
Gly Arg Asp Tyr Lys Leu Val Leu Lys Asn Gly Arg Phe Val Ala Gly
        210                 215                 220 gcg ctg gcg ctg gga ttc gtt agt ctg ccg ttg ctg gcg tgg atc gcc      720
Ala Leu Ala Leu Gly Phe Val Ser Leu Pro Leu Leu Ala Trp Ile Ala
225                 230                 235                 240 cag tcg ccg att atc atc att acc ggc gag cag ttg agc agc tat gaa      768
Gln Ser Pro Ile Ile Ile Ile Thr Gly Glu Gln Leu Ser Ser Tyr Glu
                245                 250                 255 tat ggc ttg ctg caa gtg cct att ttc ggg gcg tta att gcg ggt aac      816
Tyr Gly Leu Leu Gln Val Pro Ile Phe Gly Ala Leu Ile Ala Gly Asn
            260                 265                 270 ttg ctg tta gcg cgt ctg acc tcg cgc cgc acc gta cgt tcg ctg att      864
Leu Leu Leu Ala Arg Leu Thr Ser Arg Arg Thr Val Arg Ser Leu Ile
        275                 280                 285 att atg ggc ggc tgg ccg att atg att ggt cta ttg gtc gct gct gcg      912
Ile Met Gly Gly Trp Pro Ile Met Ile Gly Leu Leu Val Ala Ala Ala
290                 295                 300 gca acg gtt atc tca tcg cac gcg tat tta tgg atg act gcc ggg tta      960
Ala Thr Val Ile Ser Ser His Ala Tyr Leu Trp Met Thr Ala Gly Leu
305                 310                 315                 320 agt att tat gct ttc ggt att ggt ctg gcg aat gcg gga ctg gtg cga     1008
Ser Ile Tyr Ala Phe Gly Ile Gly Leu Ala Asn Ala Gly Leu Val Arg
                325                 330                 335 tta acc ctg ttt gcc agc gat atg agt aaa ggt acg gtt tct gcc gcg     1056
Leu Thr Leu Phe Ala Ser Asp Met Ser Lys Gly Thr Val Ser Ala Ala
            340                 345                 350 atg gga atg ctg caa atg ctg atc ttt acc gtt ggt att gaa atc agc     1104
Met Gly Met Leu Gln Met Leu Ile Phe Thr Val Gly Ile Glu Ile Ser
        355                 360                 365 aaa cat gcc tgg ctg aac ggg ggc aac gga ctg ttt aat ctc ttc aac     1152
Lys His Ala Trp Leu Asn Gly Gly Asn Gly Leu Phe Asn Leu Phe Asn
370                 375                 380 ctt gtc aac gga att ttg tgg ctg tcg ctg atg gtt atc ttt tta aaa     1200
Leu Val Asn Gly Ile Leu Trp Leu Ser Leu Met Val Ile Phe Leu Lys
385                 390                 395                 400 gat aaa cag atg gga aat tct cac gaa ggg taa                         1233
Asp Lys Gln Met Gly Asn Ser His Glu Gly
                405                 410

<210> SEQ ID NO 26
<211> LENGTH: 410
<212> TYPE: PRT
<213> ORGANISM: Escherichia coli

<400> SEQUENCE: 26

Met Gln Asn Lys Leu Ala Ser Gly Ala Arg Leu Gly Arg Gln Ala Leu
1               5                   10                  15

Leu Phe Pro Leu Cys Leu Val Leu Tyr Glu Phe Ser Thr Tyr Ile Gly
            20                  25                  30

Asn Asp Met Ile Gln Pro Gly Met Leu Ala Val Glu Gln Tyr Gln
        35                  40                  45

Ala Gly Ile Asp Trp Val Pro Thr Ser Met Thr Ala Tyr Leu Ala Gly
    50                  55                  60

Gly Met Phe Leu Gln Trp Leu Leu Gly Pro Leu Ser Asp Arg Ile Gly
65                  70                  75                  80
```

-continued

```
Arg Arg Pro Val Met Leu Ala Gly Val Val Trp Phe Ile Val Thr Cys
            85                  90                  95

Leu Ala Ile Leu Leu Ala Gln Asn Ile Glu Gln Phe Thr Leu Leu Arg
            100                 105                 110

Phe Leu Gln Gly Ile Ser Leu Cys Phe Ile Gly Ala Val Gly Tyr Ala
            115                 120                 125

Ala Ile Gln Glu Ser Phe Glu Glu Ala Val Cys Ile Lys Ile Thr Ala
            130                 135                 140

Leu Met Ala Asn Val Ala Leu Ile Ala Pro Leu Leu Gly Pro Leu Val
145                 150                 155                 160

Gly Ala Ala Trp Ile His Val Leu Pro Trp Glu Gly Met Phe Val Leu
            165                 170                 175

Phe Ala Ala Leu Ala Ala Ile Ser Phe Phe Gly Leu Gln Arg Ala Met
            180                 185                 190

Pro Glu Thr Ala Thr Arg Ile Gly Glu Lys Leu Ser Leu Lys Glu Leu
            195                 200                 205

Gly Arg Asp Tyr Lys Leu Val Leu Lys Asn Gly Arg Phe Val Ala Gly
            210                 215                 220

Ala Leu Ala Leu Gly Phe Val Ser Leu Pro Leu Leu Ala Trp Ile Ala
225                 230                 235                 240

Gln Ser Pro Ile Ile Ile Ile Thr Gly Glu Gln Leu Ser Ser Tyr Glu
            245                 250                 255

Tyr Gly Leu Leu Gln Val Pro Ile Phe Gly Ala Leu Ile Ala Gly Asn
            260                 265                 270

Leu Leu Leu Ala Arg Leu Thr Ser Arg Arg Thr Val Arg Ser Leu Ile
            275                 280                 285

Ile Met Gly Gly Trp Pro Ile Met Ile Gly Leu Leu Val Ala Ala Ala
            290                 295                 300

Ala Thr Val Ile Ser Ser His Ala Tyr Leu Trp Met Thr Ala Gly Leu
305                 310                 315                 320

Ser Ile Tyr Ala Phe Gly Ile Gly Leu Ala Asn Ala Gly Leu Val Arg
            325                 330                 335

Leu Thr Leu Phe Ala Ser Asp Met Ser Lys Gly Thr Val Ser Ala Ala
            340                 345                 350

Met Gly Met Leu Gln Met Leu Ile Phe Thr Val Gly Ile Glu Ile Ser
            355                 360                 365

Lys His Ala Trp Leu Asn Gly Gly Asn Gly Leu Phe Asn Leu Phe Asn
            370                 375                 380

Leu Val Asn Gly Ile Leu Trp Leu Ser Leu Met Val Ile Phe Leu Lys
385                 390                 395                 400

Asp Lys Gln Met Gly Asn Ser His Glu Gly
            405                 410
```